US012023331B2

(12) United States Patent
Snyder et al.

(10) Patent No.: US 12,023,331 B2
(45) Date of Patent: Jul. 2, 2024

(54) METHODS

(71) Applicant: INTRA-CELLULAR THERAPIES, INC., New York, NY (US)

(72) Inventors: Gretchen Snyder, New York, NY (US); Robert Davis, San Diego, CA (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 369 days.

(21) Appl. No.: 17/115,416

(22) Filed: Dec. 8, 2020

(65) Prior Publication Data

US 2021/0093634 A1    Apr. 1, 2021

Related U.S. Application Data

(63) Continuation of application No. PCT/US2019/036114, filed on Jun. 7, 2019.

(60) Provisional application No. 62/780,017, filed on Dec. 14, 2018, provisional application No. 62/682,554, filed on Jun. 8, 2018.

(51) Int. Cl.
| | | |
|---|---|---|
| A61K 31/4985 | (2006.01) | |
| A61K 45/06 | (2006.01) | |
| A61P 25/22 | (2006.01) | |
| A61P 25/24 | (2006.01) | |

(52) U.S. Cl.
CPC .......... *A61K 31/4985* (2013.01); *A61P 25/22* (2018.01); *A61P 25/24* (2018.01); *A61K 45/06* (2013.01)

(58) Field of Classification Search
CPC ... A61K 31/4985; A61K 31/519; A61P 25/22; A61P 25/24
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,767,628 A | 8/1988 | Hutchinson |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,538,739 A | 7/1996 | Bodmer et al. |
| 5,576,460 A | 11/1996 | Buchwald et al. |
| 5,648,539 A | 7/1997 | Goodbrand |
| 5,648,542 A | 7/1997 | Goodbrand et al. |
| 5,654,482 A | 8/1997 | Goodbrand |
| 5,668,801 A | 11/1997 | Mesens et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,834,493 A | 11/1998 | Gil Quintero et al. |
| 5,847,166 A | 12/1998 | Buchwald et al. |
| 5,902,901 A | 5/1999 | Goodbrand et al. |
| 6,043,370 A | 3/2000 | Kubo et al. |
| 6,166,226 A | 12/2000 | Buchwald et al. |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,419,952 B2 | 7/2002 | Wong et al. |
| 6,448,243 B1 | 9/2002 | Kitazawa et al. |
| 6,465,693 B2 | 10/2002 | Buchwald et al. |
| 6,541,639 B2 | 4/2003 | Zhou et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |

(Continued)

FOREIGN PATENT DOCUMENTS

| | | |
|---|---|---|
| GB | 1476087 | 6/1977 |
| GB | 2145422 | 3/1985 |

(Continued)

OTHER PUBLICATIONS

Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.

Angst et al. "Prevalence and Characteristics of Undiagnosed Bipolar Disorders in Patients With a Major Depressive Episode", Arch Gen Psychiatry, vol. 68(8), p. 701-709, (2011).

Bobo, et al., "Fluoxetine and olanzapine combination therapy in treatment-resistant major depression: review of efficacy and safety data", Expert Opinion on Pharmacotherapy, 10(13), pp. 2145-2159, (2009).

(Continued)

*Primary Examiner* — Sahar Javanmard

(74) *Attorney, Agent, or Firm* — Hoxie & Associates LLC

(57) ABSTRACT

The disclosure provides methods for the acute treatment of depression and/or anxiety, for the enhancement of mTOR (e.g., mTORC1) signaling, and for the reduction of neuroinflammation, comprising administering to a patient in need thereof, a therapeutically effective amount of a 5-$HT_{2A}$/mu-opioid receptor or 5-$HT_{2A}$/D1 and/or D2/mu-opioid receptor ligand.

26 Claims, No Drawings

(56) References Cited

U.S. PATENT DOCUMENTS

| | | |
|---|---|---|
| 6,762,329 B2 | 7/2004 | Marcoux et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,870 B2 | 5/2007 | Ghosh et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,309,772 B2 | 11/2012 | Weiner et al. |
| 8,461,148 B2 | 6/2013 | Hollander |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,791,138 B2 | 7/2014 | Seeman et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,179,776 B2 | 1/2019 | Davis et al. |
| 10,245,260 B2 | 4/2019 | Yao et al. |
| 10,322,134 B2 | 7/2019 | Vanover et al. |
| 10,472,359 B2 | 11/2019 | Li et al. |
| 10,533,015 B1 | 1/2020 | Tusche et al. |
| 10,597,394 B2 | 3/2020 | Yao et al. |
| 10,654,854 B2 | 5/2020 | Li et al. |
| 10,682,354 B2 | 6/2020 | Wennogle |
| 10,688,097 B2 | 6/2020 | Yao et al. |
| 10,702,522 B2 | 7/2020 | Mates et al. |
| 10,716,786 B2 | 7/2020 | Li et al. |
| 10,799,500 B2 | 10/2020 | Yao et al. |
| 10,844,061 B2 | 11/2020 | Li et al. |
| 10,899,762 B2 | 1/2021 | Mates et al. |
| 10,906,906 B2 | 2/2021 | Li et al. |
| 10,960,009 B2 | 3/2021 | Vanover et al. |
| 10,960,010 B2 | 3/2021 | Vanover et al. |
| 10,961,245 B2 | 3/2021 | Li et al. |
| 11,014,925 B2 | 5/2021 | Li et al. |
| 11,026,951 B2 | 6/2021 | Mates et al. |
| 11,052,083 B2 | 7/2021 | Li et al. |
| 11,053,245 B2 | 7/2021 | Mates et al. |
| 11,096,944 B2 | 8/2021 | Yao et al. |
| 11,124,514 B2 | 9/2021 | Mates et al. |
| 11,376,249 B2 | 7/2022 | Li et al. |
| 2001/0008942 A1 | 7/2001 | Buchwald et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0180875 A1 | 9/2004 | Lee et al. |
| 2004/0186094 A1 | 9/2004 | Robichaud et al. |
| 2004/0209864 A1 | 10/2004 | Robichaud et al. |
| 2004/0220178 A1 | 11/2004 | Robichaud et al. |
| 2005/0166771 A1 | 8/2005 | Gygi et al. |
| 2005/0182749 A1 | 8/2005 | Matsui |
| 2005/0222209 A1 | 10/2005 | Zeldis et al. |
| 2005/0239768 A1 | 10/2005 | Lee et al. |
| 2006/0128713 A1 | 6/2006 | Jolidon et al. |
| 2006/0148808 A1 | 7/2006 | Robichaud et al. |
| 2006/0178362 A1 | 8/2006 | Robichaud et al. |
| 2006/0205787 A1 | 9/2006 | Muller et al. |
| 2007/0066677 A1 | 3/2007 | Igo et al. |
| 2007/0203120 A1 | 8/2007 | McDevitt et al. |
| 2008/0069885 A1 | 3/2008 | Mesens et al. |
| 2008/0132552 A1 | 6/2008 | Kleinman et al. |
| 2008/0194592 A1 | 8/2008 | Mates et al. |
| 2008/0280941 A1 | 11/2008 | Lourtie |
| 2008/0287450 A1 | 11/2008 | Cid-Nunez et al. |
| 2009/0202631 A1 | 8/2009 | Yam et al. |
| 2010/0113781 A1 | 5/2010 | Tomesch et al. |
| 2010/0298382 A1 | 11/2010 | Seeman et al. |
| 2011/0071080 A1 | 3/2011 | Mates et al. |
| 2011/0112105 A1 | 5/2011 | Tomesch et al. |
| 2011/0269777 A1 | 11/2011 | Bachurin et al. |
| 2014/0050783 A1 | 2/2014 | Mates et al. |
| 2014/0323491 A1 | 10/2014 | Tomesch et al. |
| 2014/0364609 A1 | 12/2014 | Tomesch et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2015/0166540 A1 | 6/2015 | Mates et al. |
| 2015/0374684 A1 | 12/2015 | Javitt |
| 2016/0031885 A1 | 2/2016 | Li et al. |
| 2016/0194325 A1 | 7/2016 | Tomesch et al. |
| 2016/0194326 A1 | 7/2016 | Tomesch et al. |
| 2016/0310502 A1 | 10/2016 | Vanover et al. |
| 2017/0037048 A1 | 2/2017 | Mates et al. |
| 2017/0114037 A1 | 4/2017 | Davis et al. |
| 2017/0183350 A1 | 6/2017 | Mates et al. |
| 2017/0189398 A1 | 7/2017 | Mates et al. |
| 2017/0319580 A1 | 11/2017 | Yao et al. |
| 2019/0211015 A1 | 7/2019 | Mittelman et al. |
| 2021/0009592 A1 | 1/2021 | Li et al. |
| 2021/0093634 A1 | 4/2021 | Snyder et al. |
| 2021/0145829 A1 | 5/2021 | Li et al. |
| 2021/0163481 A1 | 6/2021 | Li et al. |
| 2022/0048910 A1 | 2/2022 | Li et al. |
| 2022/0160704 A2 | 5/2022 | Torralva |

FOREIGN PATENT DOCUMENTS

| | | |
|---|---|---|
| WO | WO 1999/043643 | 9/1999 |
| WO | WO 2000/002887 | 1/2000 |
| WO | WO 2000/064899 | 11/2000 |

OTHER PUBLICATIONS

Darmani, N. A., et al., "Do Functional Relationships Exist Between 5-HT1A and 5-HT2 Receptors?," Pharmacology and Biochemistry & Behavior, vol. 36, p. 901-906, (1990).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary p. 93.

Davis et al., "Rationale for the Development of Low Doses of ITI-007 for the Treatment of Behavioral Disturbances Associated with Dementia," The Journal of Prevention of Alzheimer's Disease,

(56) References Cited

OTHER PUBLICATIONS

2(4):302 (2015) (Clinical Trials in Alzheimer's Disease (CTAD) Congress, Symposium Summary OC51).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.
Lieberman, J.A., et al., "ITI-007 for the Treatment of Schizophrenia: A 4-Week Randomized, Double-Blind, Controlled Trial," Biol. Psychiatry, vol. 79, No. 12, pp. 952-961, (2015).
Menard, et al., "Social stress induces neurovascular pathology promoting depression," Nature Neuroscience 20: 1752-60 (2017).
Perlis et al., "Clinical Features of Bipolar Depression Versus Major Depressive Disorder in Large Multicenter Trials", Am J Psychiatry, vol. 163, p. 225-231, (2006).
Press Release, "Intra-Cellular Therapies Announces Additional Results from Phase 1/11 Clinical Trial for ITI-007 in Healthy Geriatric Subjects and Patients With Dementia," Intra-Cellular Therapies, Press Release Date: Nov. 21, 2014, (http://ir.intracellulartherapies.com/releasedetail.cfm ?ReleaseID=8 84 325), accessed on May 31, 2016.
Satlin, et al., "ITI-007 (Lumateperone) for the Treatment of Agitation in Patients with Dementia, including Alzheimer's Disease," Alzheimer's & Dementia 14(7) (Suppl.): p. 678-79 (2018) (Alzheimer's Assoc. International Conference 2018, summary of Poster p. 2-032).
Satlin, et al., "ITI-007 (Lumateperone) for the Treatment of Agitation in Patients with Dementia, including Alzheimer's Disease," Poster p. 2-032, Alzheimer's Assoc. International Conference 2018 (2018).
Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).
Vanover, et al., "Dopamine D2 receptor occupancy of lumateperone (IT1-007): a Positron Emission Tomography Study in patients with schizophrenia," Neuropsychopharmacoloirv 44:598-605, (2019).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, K., et al., "ITI-007: A Novel Therapy for the Treatment of Schizophrenia and Related Psychoses," International Clinical Psychopharamcology, vol. 26, e56, 1 page, (2011).
Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Zhang, et al., "The in vivo effects of olanzapine and other antipsychotic agents on receptor occupancy and antagonism of dopamine D1, D2, D3, 5HT2A and muscarinic receptors", Psychopharmacology, vol. 141, pp. 267-278, (1999).
Bundel, et al., "Dopamine D2 receptors gate generalization of conditioned threat responses through Mtorc1 signaling in the extended amygdala," Mol. Psychiatry, 21(11): 1545-1553 (2016).
Davis et al., "ITI-007 in the treatment of schizophrenia: from novel pharmacology to clinical outcomes," Expert Review of Neurotherapeutics, vol. 16, No. 6, pp. 601-614 (2016).
Davis, et al. "ITI-007 demonstrates brain occupancy at serotonin 5-HT2A and dopamine D2 receptors and serotonin transporters using positron emission tomography in healthy volunteers", Psychopharmacology, vol. 232:2863-2872,(2015).
Harvey, B.H., et al., "Serotonin and Stress: Protective or Malevolent Actions in the Biobehavioral Response to Repeated Trauma?" Annals of the New York Academy of Sciences, vol. 1032, p. 267-272; DOI: 10.1196/annals.1314.035 (2004).
Kessler, R.C., et al., "Lifetime Prevalence and Age-of-Onset Distributions of DSM-IV Disorders in the National Comorbidity Survey Replication", Arch Gen Psychiatry; vol. 62, p. 593-602, (2005).
Khorana, N., et al., "Gamma-Carbolines: Binding at 5-HT5A Serotonin Receptors", Bioorganic & Medicinal Chemistry, vol. 11, pp. 717-722, p. 718 Table 1, (2003).
Lee, T., et al. "Novel, Highly Potent, Selective 5-HT2A/D2 Receptor Antagonists as Potential Atypical Antipsychotics," Bioorg. Med. Chem. Lett. vol. 13, pp. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).
Lin, Y-T., et al., "Dosage and Duration of Antipsychotic Treatment in Demented Outpatients with Agitation or Psychosis," Journal of the Formosan Medical Association, vol. 114, pp. 147-153, (2015).
Marek, G.J., et al., "Synergistic Action of 5-HT2A Antagonists and Selective Serotonin Reuptake Inhibitors in Neuropsychiatric Disorder," Neuropsychopharmacology, vol. 28, pp. 402-412 (2003).
Noble, F., et al., "The opioid receptors as targets for drug abuse medication," British Journal of Psychology, vol. 172, pp. 3964-3979, (2015).
Pine, A., et al., "Dopamine, Time, and Impulsivity in Humans," The Journal of Neuroscience, vol. 30, pp. 8888-8896, (2010).
Pubchem, CID-22036753, p. 4, pp. 1-12 (2007).
Pubchem, CID-9953107, p. 3, pp. 1-9 (2006).
Pubchem, CID-103920954 pp. 1-6 (2011).
Rainer, M.K., "Risperidone long-acting injection: a review of its long term safety and efficacy," Neuropsychiatric Disease and Treatment, vol. 4, No. 5, pp. 919-927 (2008).
Renner, J.A., Jr., "Management of Psychiatric Medications in Patients Receiving Buprenorphine/Naloxone," PCSS MAT Training Providers' Clinical Support System for Medical Assisted Treatment, Last Updated: Nov. 28, 2013, 4 pages.
Sem LA, et al., "Off-Label Prescribing of Second-Generation Antipsychotics to Elderly Veterans with Posttraumatic Stress Disorder and Dementia," J. Am. Geriatr. Soc., vol. 65, pp. 1789-1795, (2017); DOI: 10.1111/iirs.14897.
Snyder, G.L., et al., "Functional profile of a novel modulator of serotonin, dopamine, and glutamate neurotransmission," Psychopharmacology, vol. 232, p. 605-621 (2015) Published online Aug. 2014, DOI 10.1007/s00213-014-3704-1.
Taragano, F.E., et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).
Weschules, D., et al., "Acetylcholinesterase Inhibitor and N-Methyl-D-Aspartic Acid Receptor Antagonist Use among Hospice Enrollees with a Primary Diagnosis of Dementia", Journal of Palliative Medicine, vol. 11, No. 5, pp. 738-745 (2008).
Zhang, G., et al., "The role of serotonin 5-HT2A receptors in memory and cognition," frontiers in Pharmacology, vol. 6, Article 225, (2015).
Intra-Cellular Therapies, Inc., "Corporate Presentation" (Sep. 24, 2019), downloaded from https://ir.intracellulartherapies.com/static-files/93608960-f01c-4864-aa22-8cadb3539753 (last accessed Mar. 13, 2023).
Calabrese et al., "Efficacy and Safety of Lumateperone for Major Depressive Episodes Associated with Bipolar I or Bipolar II Disorder: A Phase 3 Randomized Placebo-Controlled Trial," *American Journal of Psychiatry*, 178(12):1098-1106 (Dec. 2021).
Kudla, et al., "Influence of G protein-biased agonists of μ-opioid receptor on addiction-related behaviors," *Pharmacol Rep.*, 73(4), pp. 1033-1051, (2021).

(56) References Cited

OTHER PUBLICATIONS

McIntyre, R.S., "Rapid-acting antidepressants in psychiatry: psychedelics, episodic treatments, innovation, and clarion call for methodologic rigor in drug development," *Expert Opinion on Drug Safety*, 21(6):715-716 (2022).

Puig et al., "Serotonin and Prefrontal Cortex Function: Neurons, Networks, and Circuits," Mol Neurobiol., 44(3), p. 449-464, (2011).

Torralva, et al., "Fentanyl but not Morphine Interacts with Nonopioid Recombinant Human Neurotransmitter Receptors and Transporters," *J Pharmacol Exp Ther.*, 374(3), pp. 376-391, (2020).

Wang et al., "Rapid-acting antidepressants targeting modulation of the glutamatergic system: clinical and preclinical evidence and mechanisms," *General Psychiatry*, 35e100922 (2022).

Witkin et al., "Chapter 3: Rapid-acting Antidepressants," Advances in Pharmacology, vol. 86, 50 pages, (2019).

METHODS

CROSS-REFERENCE TO RELATED APPLICATIONS

This application is a U.S. continuation application filed under 35 U.S.C. § 111(a) claiming priority to International Application No. PCT/US2019/036114 filed on Jun. 7, 2019, which claims benefit to and priority from U.S. Provisional Applications No. 62/682,554, filed on Jun. 8, 2018, and 62/780,017, filed on Dec. 14, 2018, the contents of each of which are hereby incorporated by reference in their entireties.

TECHNICAL FIELD

The present disclosure relates to use of a 5-HT$_{2A}$/mu-opioid receptor or 5-HT$_{2A}$/D1 and/or D2/mu-opioid receptor ligand, for example, a substituted heterocycle fused gamma-carboline, as described herein, in free, pharmaceutically acceptable salt or prodrug form, for acute treatment of depression and anxiety, and/or symptoms related thereto.

BACKGROUND OF THE INVENTION

Substituted heterocycle fused gamma-carbolines are known to be agonists or antagonists of 5-HT$_2$ receptors, particularly 5-HT$_{2A}$ and 5-HT$_{2C}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-HT$_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. PCT/US08/03340 (WO 2008/112280), and its U.S. equivalent US 2010/113781, and U.S. application Ser. No. 10/786,935 (published as US 2004/209864) also disclose methods of making substituted heterocycle fused gamma-carbolines and uses of these gamma-carbolines as serotonin receptor agonists and antagonists useful for the control and prevention of central nervous system disorders such as addictive behavior and sleep disorders.

Some substituted heterocycle fused gamma-carbolines are known to be 5-HT$_{2A}$/mu-opioid receptor or 5-HT$_{2A}$/D1 and/or D2/mu-opioid receptor ligands, which are useful in treating central nervous system disorders. These compounds antagonize the serotonin-2A (5-HT$_{2A}$) receptor, and modulate activity at the mu-opioid receptor, and/or modulate dopamine receptor signaling at the level of key intra-cellular phosphoproteins. Such compounds are principally known to be useful for the treatment of substance abuse disorders and pain disorders.

Some of such compounds may act as both post-synaptic antagonists and pre-synaptic partial agonists at D1 and/or D2 receptors. They may also stimulate phosphorylation of glutamatergic NMDA NR2B, or GluN2B, receptors in a mesolimbic specific manner. It is believed that this regional selectivity in the brain areas thought to mediate the efficacy of antipsychotic drugs, together with the serotonergic, glutamatergic, and dopaminergic interactions, may result in antipsychotic efficacy for positive, negative, affective and cognitive symptoms associated with schizophrenia. The compounds also exhibit serotonin reuptake inhibition, providing antidepressant activity for the treatment of schizoaffective disorder, co-morbid depression, and/or as a stand-alone treatment for major depressive disorder. These compounds display differential dose-dependent effects, selectively targeting the 5-HT$_{2A}$ receptor at low doses, while progressively interacting with the dopamine receptors (D1 and/or D2) at higher doses.

Lumateperone, having the formula:

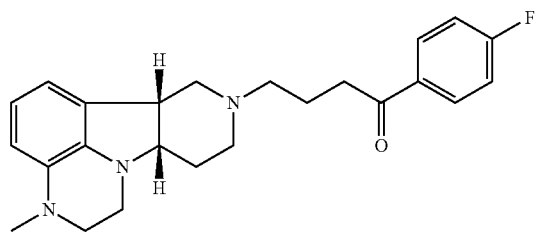 [SMILES: CN1CCN2c3c(cccc31)[C@@H]1CN(CCCC(=O)c3ccc(F)cc3)CC[C@@H]12]

is a novel therapeutic agent with potent (Ki=0.5 nM) 5-HT$_{2A}$ receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone is in Phase III clinical development as a treatment for schizophrenia, bipolar depression and agitation in dementia, including Alzheimer's Disease.

Lumateperone and related compounds have been disclosed in U.S. Pat. Nos. 6,548,493; 7,238,690; 6,552,017; 6,713,471; U.S. RE39680, and U.S. RE39679, as novel compounds useful for the treatment of disorders associated with 5-HT$_{2A}$ receptor modulation such as anxiety, depression, psychosis, schizophrenia, sleep disorders, sexual disorders, migraine, conditions associated with cephalic pain, and social phobias. PCT/US08/03340 and U.S. Pat. No. 7,081,455 also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/145900 and U.S. Pat. No. 8,598,119, and WO 2013/155506 and US 2015/0080404, each incorporated herein by reference, disclose the use of specific substituted heterocycle fused gamma-carbolines for the treatment of a combination of psychosis and depressive disorders as well as sleep, depressive and/or mood disorders in patients with psychosis or Parkinson's disease and for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia. WO 2009/114181 and U.S. Pat. No. 8,648,077, each incorporated herein by reference, disclose methods of preparing toluenesulfonic acid addition salt crystals of particular substituted heterocycle fused gamma-carbolines, e.g., toluenesulfonic acid addition salt of 4-((6bR,10aS)-3-methyl-2,3,6b,9,10,10a-hexahydro-1H-pyrido[3',4': 4,5] pyrrolo[1,2,3-de]quinoxalin-8(7H)-yl)-1-(4-fluorophenyl)-1-butanone.

WO 2011/133224 and U.S. Pat. No. 8,993,572, each incorporated herein by reference, disclose prodrugs/metabolites of substituted heterocycle fused gamma-carboline for improved formulation, e.g., extended/controlled release formulation. This application discloses that heterocycle fused gamma-carbolines N-substituted with a 4-fluorophenyl(4-hydroxy)butyl moiety are shown to have high selectivity for the serotonin transporter (SERT) relative to the heterocycle fused gamma-carboline containing 4-fluorophenylbutanone.

WO 2009/145900 (and U.S. Pat. No. 8,598,119) teaches that selected substituted heterocycle fused gamma-carboline compounds have nanomolar affinity for the serotonin reuptake transporter (SERT) and so are selective serotonin reuptake inhibitors.

As disclosed in WO2015/154025, US 2017/0183350, and WO 2017/165843 (and U.S. application Ser. No. 16/088,397), each incorporated herein by reference, deuterated forms of lumateperone and related compounds have been shown to have improved metabolic stability.

The compounds described in the present disclosure have been disclosed in WO 2017/132408 (and also US 2017/0319580, the contents of which are incorporated by reference) as unexpectedly having potent activity at serotonin receptors (e.g., 5-HT$_{2A}$), serotonin transporters (SERT), dopamine receptors (e.g., D1 and/or D2), and Mu-opiate receptors. It has further been found that these compounds display the unique Mu-opiate receptor activity of a biased ligand. As described herein, it is further believed that the compounds of the present disclosure, via their D1 receptor activity, may also produce enhanced NMDA and AMPA mediated signaling through the mTOR pathway.

Conventional antidepressants often take weeks or months to achieve their full effects. For example, selective serotonin reuptake inhibitors (SSRIs), such as sertraline (Zoloft, Lustral), escitalopram (Lexapro, Cipralex), fluoxetine (Prozac), paroxetine (Seroxat), and citalopram, are considered first line therapies for depression, including major depressive disorder, due to their relatively mild side effects and broad effect on the symptoms of depression and anxiety. SSRIs, however, are generally not effective right away, and so are not particularly useful for acute treatment of depression. This delayed onset of action increases the risk for suicidal behavior. Benzodiazepines can be used for acute treatment of anxiety but can be addictive and have a high risk of overdose. Ketamine has recently been tested as a rapid-acting antidepressant for treatment-resistant depression, in bipolar disorder and major depressive disorder, but it has significant side effects and risk of overdose, and it is not orally active.

Over the last twenty years, at least six placebo-controlled clinical trials have studied ketamine as a rapid-acting antidepressant. In one study by Berman et al., involving 23 to 56-year old patients with major depressive episodes, it was found that a 40-minute infusion of ketamine at a total dose of 0.5 mg/kg resulted in significantly improved ratings on the Hamilton Depression Rating Scale (HDRS) compared to placebo after only 24 hours. Similar results were shown by Zarate et al. in 2006. Ketamine's effects begin as early 4 hours after intravenous infusion and can persist for up to 2 weeks. However, ketamine's approved medical uses are limited because of side effects, including perceptual disturbances, anxiety, dizziness, feelings of depersonalization and even psychosis (and it is a schedule III drug carrying risks of addiction and abuse). Ketamine also produces dissociative effects, such as hallucination and delirium, as well as analgesia and amnesia, none of which are associated with traditional antidepressants. These dissociative and other effects appear to be mediated by distinct cellular pathways from those which mediate the antidepressant effects of ketamine.

Unlike traditional antidepressants, which predominantly operate within the monoamine neurotransmitter sphere (i.e., serotonin, norepinephrine, and dopamine), ketamine is a selective NMDA receptor antagonist. The most widely prescribed current anti-depressants are SSRIs, monoamine oxidase inhibitors, and tricyclic antidepressants (primarily serotonin uptake, norepinephrine uptake, and/or dopamine uptake inhibitors). Ketamine acts through a separate system unrelated to the monoamines, and this is a major reason for its much more rapid effect. Ketamine directly antagonizes extrasynaptic glutamatergic NMDA receptors, which also indirectly results in activation of AMPA-type glutamate receptors. The downstream effects involve the brain-derived neurotrophic factor (BDNF) and mTOR (e.g., mTORC1) kinase pathways (signal transduction pathways).

Animal studies of depression have shown a link to reduction of mTOR (e.g., mTORC1) expression or activity. mTOR is a serine/threonine and tyrosine kinase which is a member of the phosphatidyl inositol 3-kinase family (PI3K family). It operates as a major component of the mTOR complex 1 (mTORC1) and the mTOR complex 2 (mTORC2). The mTOR pathways are central regulators of mammalian metabolism and physiology, with impacts on cell growth and survival, cytoskeleton organization, synaptic plasticity, memory retention, neuroendocrine regulation and neuronal recovery from stress (e.g. hypoxic stress). Studies have shown that activation of mTOR signaling reverses some of the synaptic and behavioral deficits caused by stressors, including chronic stress. There is evidence suggesting that ketamine's anti-depressant effects may be mediated through its activation of mTOR signaling (in combination with its promotion of the release of stored BDNF). Research has shown that a single antidepressant-effective dose of ketamine can induce a rapid-onset (within 30 minutes of administration) induction of phospho-mTOR, as well as phospho-p70S6 kinase and phosphor-4EBP176, 177, in the prefrontal cortex and hippocampus of mice and rats. This suggests a mechanism whereby ketamine-induced protein translation occurs in an mTOR activation-dependent manner.

Ketamine (S-ketamine, or esketamine) was recently approved by the U.S. Food & Drug Administration (FDA) as a new treatment for treatment-resistant depression in adults (trade name Spravato). However, the approval came with several strict requirements and restrictions due to the observance of potentially severe side effects with ketamine treatment. For example, the FDA only approved Spravato for treatment in conjunction with an oral antidepressant, not as monotherapy, and requires that the drug be administered once or twice per week under the direct supervision of a healthcare provider. Moreover, patients are required to remain under observation for 2 hours after each dose, in order to watch for the most dangerous side effects—sedation, disassociation, and hypertension. Clinical studies also suggest a high risk of abuse and suicidal ideation.

New, fast-acting methods for the acute treatment of depression are urgently needed.

BRIEF SUMMARY OF THE INVENTION

The particular substituted heterocycle fused gamma-carbolines as described herein are believed to exhibit a fast-acting antidepressant action via indirect dopamine D1 receptor-dependent enhancement of NMDA and AMPA currents coupled with activation of the mTOR (e.g., mTORC1) signaling pathway, and paralleled by anti-inflammatory properties. Such compounds may thus be useful as orally-available, rapid-acting treatments for depression and anxiety, alone or in conjunction with other anti-anxiety or anti-depressant drugs. Such compounds should lack the adverse side effects of ketamine and other current pharmacological approaches to depression. In contrast to traditional treatments for depression, such as SSRIs, which typically have an onset of action 3-4 weeks after initiation of daily dosing, the unique pharmacological profile of the compounds described herein are predicted to result in immediate onset of action (e.g., hours to days after initial dosing). In addition, unlike benzodiazepine class agents, the compounds described herein appear to be non-addictive. They are therefore particularly suitable for the treatment of acute depressive episodes, including suicidal ideation and severe acute depression and/or severe acute anxiety.

The present disclosure thus provides a method for the acute treatment of depression and/or anxiety comprising administering an effective amount of a 5-HT$_{2A}$/mu-opioid receptor or 5-HT$_{2A}$/D1 and/or D2/mu-opioid receptor ligand, for example, a substituted heterocycle fused gamma-carboline, as described herein, in free, pharmaceutically acceptable salt or prodrug form, to a patient in need thereof. The present disclosure further provides a method for enhancing mTOR signaling, e.g., in the brain, comprising administering an effective amount of a 5-HT$_{2A}$/mu-opioid receptor or 5-HT$_{2A}$/D1 and/or D2/mu-opioid receptor ligand, for example, a substituted heterocycle fused gamma-carboline, as described herein, in free, pharmaceutically acceptable salt or prodrug form, to a patient in need thereof. The present disclosure further provides a method for reducing neuroinflammation, e.g., in the brain, comprising administering an effective amount of a 5-HT$_{2A}$/mu-opioid receptor or 5-HT$_{2A}$/D1 and/or D2/mu-opioid receptor ligand, for example, a substituted heterocycle fused gamma-carboline, as described herein, in free, pharmaceutically acceptable salt or prodrug form, to a patient in need thereof.

In some embodiments, the present disclosure provides the above methods, wherein such methods further comprise the concurrent administration of a PDE1 inhibitor, for example, the compounds of Formula II, as disclosed herein. Such compounds are disclosed in, for example, U.S. Pat. No. 9,545,406, the contents of which is hereby incorporated by reference in its entirety, as having utility in the treatment of central nervous system diseases, disorders and injuries, and as neuroprotective and/or neural regenerative agents. Such compounds are further disclosed in, for example, WO 2018/049417, the contents of which is hereby incorporated by reference in its entirety, as having utility in the treatment of diseases and disorders characterized by neuroinflammation.

DETAILED DESCRIPTION

The compound of Formula A, also known as lumateperone, is shown below:

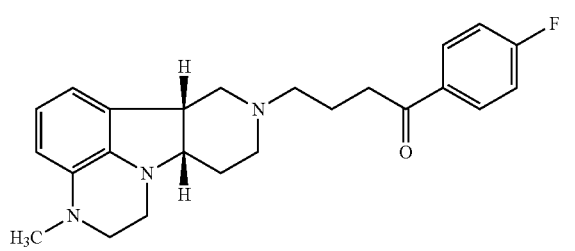

Formula A

The compound of Formula A is known to provide effective treatment of 5-HT$_{2A}$, SERT and/or D2 receptor related disorders without significant extrapyramidal side effects, as similarly disclosed and claimed in WO 2009/145900 and US 2011/0071080, the contents of which are incorporated by reference in their entirety. Although similar in structure, the compounds of Formula I have been unexpectedly found to have potent activity as antagonists of the μ-opioid receptor. This is unexpected because the compound of Formula A has not been known or understood to have any μ-opioid receptor activity or binding.

Compounds according to Formula I, particularly wherein X is —NH, and L is O, demonstrate potent binding to the 5-HT$_{2A}$, D$_1$ and Mu opiate receptors, along with moderate binding to the D2 and SERT receptors. Functionally, such binding can generally result in either agonist activity, partial agonist activity, or antagonist activity. The compounds according to Formula I produce antagonist activity at the 5-HT$_{2A}$ and SERT receptors, and mixed agonist/antagonist activity at the D$_1$, D2 and mu-opiate receptors (depending on cell type). Furthermore, it has been unexpectedly found that such compounds may operate as "biased" Mu opiate ligands. This means that when the compounds bind to Mu opiate receptors, they may operate as partial Mu agonists via G-protein coupled signaling, but as Mu antagonists via beta-arrestin signaling. This is in contrast to the traditional opiate agonists morphine and fentanyl, which tend to strongly activate both G-protein signaling and beta-arrestin signaling pathways. The activation of beta-arrestin signaling by such drugs is thought to mediate the gastrointestinal dysfunction and respiratory suppression typically mediated by opiate drugs. Compounds according to Formula I are therefore expected to provide anti-depressant and anxiolytic activity, as well as pain relief, in patients suffering from acute depression or anxiety co-morbid with a pain disorder, with less severe gastrointestinal and respiratory side effects than existing opiate analgesics could provide. Furthermore, the Compounds of the present disclosure also have sleep maintenance effect due to their serotonergic activity. As many people suffering from chronic pain, depression and/or anxiety have difficulty sleeping, these compounds can help such patients sleep through the night due to the synergistic effects of serotonergic and opiate receptor activities.

Low doses of an antipsychotic drug (APD) enhance the effectiveness of antidepressants in patients suffering from treatment-resistant depression (TRD) (Tohen et al., 2010). At the molecular level, combined application of low concentrations of antipsychotic drugs with selective serotonin uptake inhibitors (SSRIs) robustly and synergistically increase the activity of NMDA receptors on pyramidal neurons in the medial prefrontal cortex (mPFC). Further, combined application of an APD with an SSRI enhances AMPA receptor currents in the mPFC—an effect not seen with either treatment alone. Interestingly, this enhancement of glutamatergic neurotransmission in mPFC via both NMDA and AMPA receptors is mimicked by non-anesthetic doses of ketamine, an agent which provides rapid antidepressant efficacy in patients with TRD. Together, this data indicates that a combination of APD and SSRI properties is effective for alleviating TRD.

Compounds disclosed herein possess a highly unique combination of properties which shares some overlap with each of APD agents, SSRI agents and opiate agents (both agonists and antagonists). It is further believed that these compounds also enhance glutamatergic neurotransmission by effects on both NMDA and AMPA receptor conductance in the medial prefrontal cortex (mPFC) of the brain. Such actions would be consistent with the effects of other rapid-acting antidepressant therapies, including the combined use of olanzapine (a D2-receptor antagonist APD) with fluoxetine (an SSRI) and of ketamine, and further adding the pain-relief and anxiety-relief aspects of an opiate.

In a particular embodiment, the present disclosure provides a method (Method 1) for the acute treatment of depression and/or anxiety comprising administering to a patient in need thereof, a therapeutically effective amount of a 5-HT$_{2A}$/mu-opioid receptor or 5-HT$_{2A}$/D1 and/or D2/mu-opioid receptor ligand, for example, a compound of Formula I:

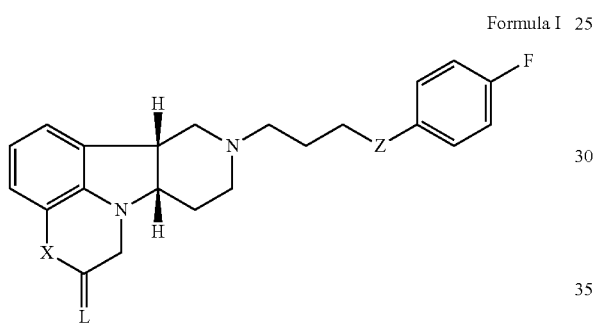

Formula I wherein:

X is —N(H)—, —N(CH$_3$)— or —O—;

L is selected from O, NH, NR$^a$, and S

Z is —O—;

R$_a$ is H or C$_{1-4}$alkyl;

optionally in deuterated form, in free, pharmaceutically acceptable salt or prodrug form. For example, Method 1 may be as follows:

1.1. Method 1, wherein X in the compound of Formula I is —N(H)— or —O—;
1.2. Method 1 or 1.1, wherein X in the compound of Formula I is —N(H);
1.3. Method 1 or 1.1, wherein X in the compound of Formula I is —N(CH$_3$)—;
1.4. Method 1 or 1.1, wherein X in the compound of Formula I is —O—;
1.5. Method 1 or any of formulae 1.1-1.4, wherein L in the compound of Formula I is O;
1.6. Method 1 or any of formulae 1.1-1.4, wherein L in the compound of Formula I is NH or NR$^a$;
1.7. Method 1 or any of formulae 1.1-1.4, wherein L in the compound of Formula I is S;
1.8. Method 1 or any of formulae 1.1-1.4, wherein the compound of Formula I is:

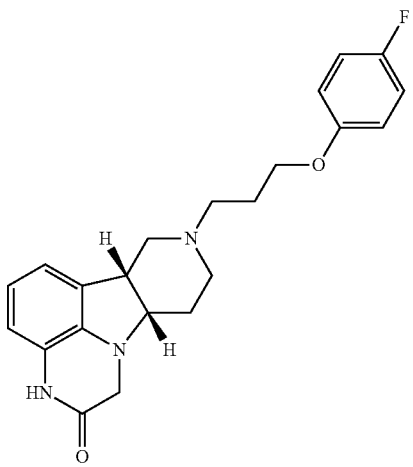 [SMILES: O=C1CN2c3c(cccc3[C@@H]3CN(CCCOc4ccc(F)cc4)CC[C@@H]32)N1]

1.9. Any of Method 1 or 1.1-1.8, wherein the Compound of Formula I is in the form of the tosylate salt;
1.10. Any of Method 1 or 1.1-1.9, wherein the Compound of Formula I is in the form of the free base;
1.11. Method 1 or any of 1.1-1.10 wherein the Compound of Formula I is in deuterated form, e.g., wherein the deuterium:protium ratio for a specified carbon-bound hydrogen atom is significantly higher, e.g., at least 2λ, for example at least 10× higher, than the natural isotope ratios;
1.12. Method 1.11, wherein the Compound of Formula I is:

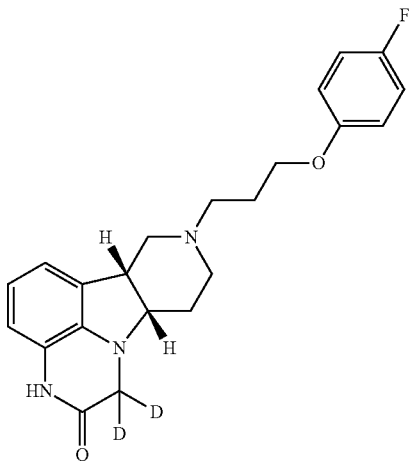

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free or pharmaceutically acceptable salt form, e.g. tosylate salt form;
1.13. Any foregoing method, wherein the 5-HT$_{2A}$/mu-opioid receptor or 5-HT$_{2A}$/D1 and/or D2/mu-opioid receptor ligand is a compound of Formula I in tosylate salt form, administered in a daily dose equivalent to 1 to 100 mg of free base, e.g., 1 to 75 mg, or 1 to 60 mg, or 1 to 40 mg, or 1 to 20 mg, or 1 to 10 mg, of free base;

1.14. Method 1.13 wherein the method comprises once daily administration of a unit dosage for oral administration, for example a tablet or capsule, comprising the compound of Formula I in tosylate salt form in an amount equivalent 1 to 100 mg of free base, e.g., 1 to 75 mg, or 1 to 60 mg, or 1 to 40 mg, or 1 to 20 mg, or 1 to 10 mg, of free base, and a pharmaceutically acceptable diluent or carrier;

1.15. Method 1.13 wherein the method comprises once daily administration of a unit dosage for subcutaneous or transmucosal administration, e.g., a sublingual or buccal orally disintegrating tablet or film, comprising the compound of Formula I in tosylate salt form in an amount equivalent to 0.5 to 30 mg of free base, e.g., 1-10 mg of free base, and a pharmaceutically acceptable diluent or carrier;

1.16. Any foregoing method wherein the condition to be treated is alleviated within one week, e.g., within three days, e.g., within one day;

1.17. Any foregoing method wherein the patient is diagnosed as having suicidal ideation and/or suicidal tendencies;

1.18. Any foregoing method wherein the condition to be treated is acute anxiety (e.g., a short-duration anxious episode associated with generalized anxiety disorder, panic disorder, specific phobias, or social anxiety disorder, or social avoidance);

1.19. Any foregoing method wherein the condition to be treated is acute depression (e.g., acute major depressive episode, acute short-duration depressive episode, acute recurrent brief depressive episode);

1.20. Any foregoing method wherein the condition to be treated is treatment resistant depression (e.g., depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);

1.21. Any foregoing method wherein the condition to be treated is selected from bipolar depression and major depressive disorder;

1.22. Any foregoing method wherein the 5-HT$_{2A}$/mu-opioid receptor or 5-HT$_{2A}$/D1 and/or D2/mu-opioid receptor ligand is in combination (e.g. a fixed combination in a unit dosage form, or a free combination administered sequentially or simultaneously or within a 24-hour period) with an effective amount of an additional anxiolytic or antidepressant agent;

1.23. Method 1.22 wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:
(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
(c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

1.24. Any foregoing method, wherein the method enhances mTOR (e.g., mTORC1) signaling (e.g., in the hippocampus, or in the brain, or in the pre-frontal cortex, or in the mPFC);

1.25. Any foregoing method wherein the method reduces neuroinflammation (e.g., by suppressing pro-inflammatory cytokine expression [IL-1β, IL-6, TNF-α, CCL2] and/or by enhancing anti-inflammatory cytokine expression [IL-4, IL-10]);

1.26. Method 1.25, wherein the neuroinflammation is caused by an infectious agent, e.g., a gram-negative bacterium (e.g., meningococcal meningitis);

1.27. Any foregoing method, wherein the compound of Formula I is administered intra-nasally, subcutaneously, intravenously, orally, or sub-lingually, or intraperitoneally or buccally;

1.28. Any foregoing method, wherein the 5-HT$_{2A}$/mu-opioid receptor or 5-HT$_{2A}$/D1 and/or D2/mu-opioid receptor ligand is administered to the patient concurrently with a PDE1 (cyclic nucleoside phosphodiesterase 1) inhibitor (e.g., administered simultaneously, separately or sequentially), in free or pharmaceutically acceptable salt form;

1.29. Method 1.28, wherein the PDE1 inhibitor is a compound according to Formula II:

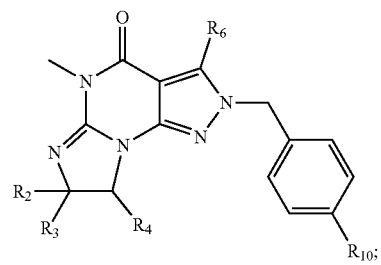

1.30. Method 1.29, wherein, in the Compound of Formula II, $R_6$ is phenylamino or 4-fluorophenylamino;
1.31. Method 1.29, wherein, in the Compound of Formula II, $R_{10}$ is 3-fluoropyrid-2-yl or methylcarbonyl;
1.32. Method 1.29, wherein, in the Compound of Formula II, $R_6$ is phenylamino or 4-fluorophenylamino and $R_{10}$ is 3-fluoropyrid-2-yl or methylcarbonyl;
1.33. Any Methods 1.29-1.32, wherein the Compound of Formula II is

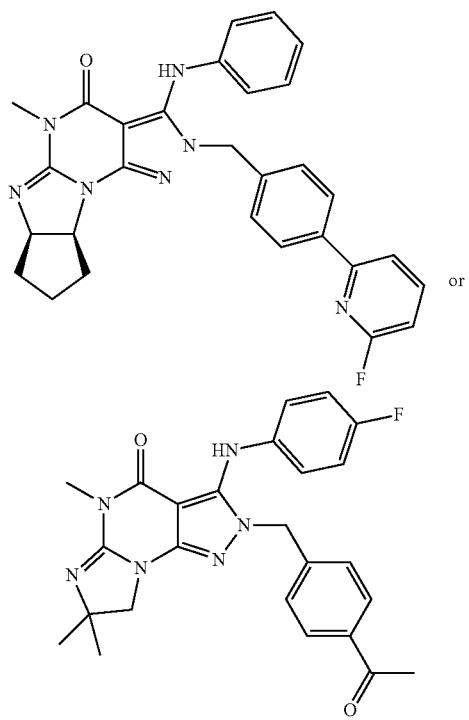

or

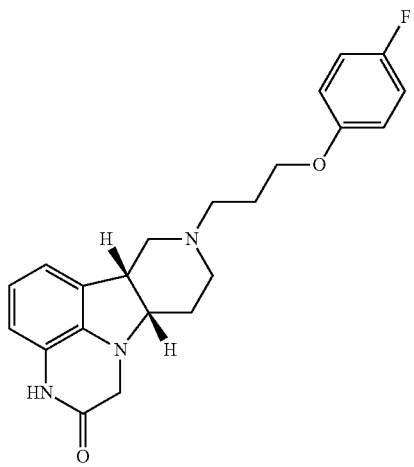 [SMILES: O=C1CN2c3c(cccc3[C@@H]3CN(CCCOc4ccc(F)cc4)CC[C@@H]32)N1]

in free or pharmaceutically acceptable salt form.
1.34 Method 1.33, wherein the Compound of Formula II is in the form of the monophosphate salt;
1.35 Any of Methods 1.29-1.34, wherein the Compound of Formula I is:

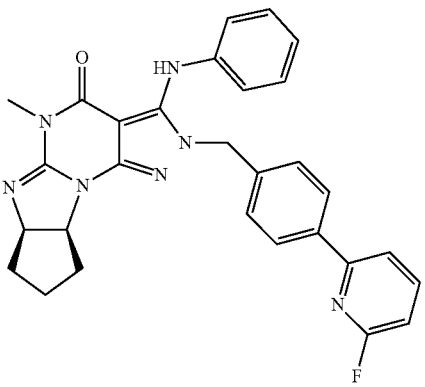 [SMILES: Cn1c(=O)/c(=C(/NCc2ccc(-c3cccc(F)n3)cc2)Nc2ccccc2)c(=N)n2c1=N[C@@H]1CCC[C@@H]12]

in free or pharmaceutically acceptable salt form, e.g., tosylate salt form; and the Compound of Formula II is:

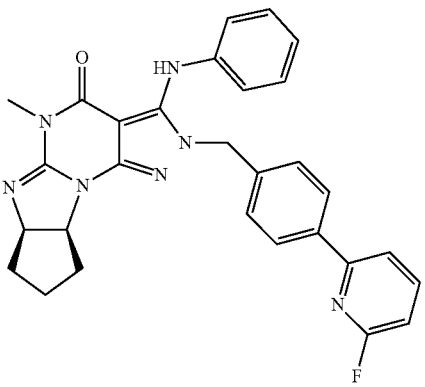 [SMILES: Cn1c(=O)/c(=C(/NCc2ccc(-c3cccc(F)n3)cc2)Nc2ccccc2)c(=N)n2c1=N[C@@H]1CCC[C@@H]12]

in free or pharmaceutically acceptable salt form, e.g., monophosphate salt form;
1.36 Any of Methods 1.29-1.35, comprising administration of a pharmaceutical composition comprising effective amounts of both a Compound of Formula I and a Compound of Formula II;
1.37 Any foregoing method, wherein the method further comprises the concurrent administration of another anti-depressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;
1.38 Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;
1.39 Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;
1.40 Any foregoing method, wherein the method provides the patient with an acute response to treatment with the therapeutic agent or agents (e.g., the Compound of Formula I, or the combination of the Compound or Formula I and the Compound of Formula II, and any additional antidepressant agents);
1.41 Method 1.40, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours);
1.42 Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a nor-epinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

1.43 Any foregoing method, wherein the anxiety or depression is not associated with schizophrenia or dementia;

1.44 Any foregoing method, wherein the patient does not suffer from (or has not been diagnosed with) schizophrenia or dementia;

1.45 Any foregoing method, wherein the 5-HT$_{2A}$/mu-opioid receptor or 5-HT$_{2A}$/D1 and/or D2/mu-opioid receptor ligand has an IC$_{50}$ of less than 250 nM or an EC$_{50}$ of less than 250 nM for activity (agonism and/or antagonism) at the 5-HT$_{2A}$ receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.46 Any foregoing method, wherein the 5-HT$_{2A}$/mu-opioid receptor or 5-HT$_{2A}$/D1 and/or D2/mu-opioid receptor ligand has an IC$_{50}$ of less than 250 nM or an EC$_{50}$ of less than 250 nM for activity (agonism and/or antagonism) at the mu-opioid receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.47 Any foregoing method, wherein the 5-HT$_{2A}$/D1 and/or D2/mu-opioid receptor ligand has an IC$_{50}$ of less than 250 nM or an EC$_{50}$ of less than 250 nM for activity (agonism and/or antagonism) at the D1 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.48 Any foregoing method, wherein the 5-HT$_{2A}$/D1 and/or D2/mu-opioid receptor ligand has an IC$_{50}$ of less than 250 nM or an EC$_{50}$ of less than 250 nM for activity (agonism and/or antagonism) at the D2 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.49 Any foregoing method, wherein the 5-HT$_{2A}$/mu-opioid receptor or 5-HT$_{2A}$/D1 and/or D2/mu-opioid receptor ligand has an IC$_{50}$ of less than 250 nM or an EC$_{50}$ of less than 250 nM for activity (agonism and/or antagonism) at the serotonin transporter (SERT), e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

1.50 Any foregoing method, wherein the 5-HT$_{2A}$/mu-opioid receptor or 5-HT$_{2A}$/D1 and/or D2/mu-opioid receptor ligand is a biased ligand at the mu-opioid receptor;

1.51 Any foregoing method, wherein the 5-HT$_{2A}$/mu-opioid receptor or 5-HT$_{2A}$/D1 and/or D2/mu-opioid receptor ligand is a compound of Formula I, e.g., in tosylate salt form, administered in the form of a long-acting injectable (LAI) composition, e.g., for intramuscular or subcutaneous injection;

1.52 Method 1.51, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

1.53 Method 1.51 or 1.52, wherein the LAI composition comprises the compound of Formula I dissolved, dispersed, suspended, or encapsulated in a polymeric matrix;

1.54 Method 1.53, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

1.55 Method 1.54, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, poly (alkyl alpha-cyanoacrylate) such as poly(butyl cyanoacrylate) or poly(2-octyl cyanoacrylate), poly(ortho ester), polycarbonate, polyortho-carbonate, a polyamino acid, (for example poly-gamma.-L-alanine, poly-.gamma.-benzyl-L-glutamic acid or poly-y-methyl-L-glutamic acid), and/or hyaluronic acid ester;

1.56 Method 1.55, wherein the one or more polymers comprises polylactic acid, polyglycolic acid, polycitric acid, polymalic acid, or a poly(lactic acid-glycolic acid) copolymer;

1.57 Method 1.55, wherein the one or more polymers comprises a poly(lactic acid-glycolic acid) copolymer, e.g., poly-d,l-lactide-co-glycolide;

1.58 Any foregoing method, wherein the 5-HT$_{2A}$/mu-opioid receptor or 5-HT$_{2A}$/D1 and/or D2/mu-opioid receptor ligand is administered as monotherapy, e.g., it is not administered concurrently or in conjunction with an anti-depressant, anti-psychotic, or anti-anxiety agent;

1.59 Any foregoing method, wherein the 5-HT$_{2A}$/mu-opioid receptor or 5-HT$_{2A}$/D1 and/or D2/mu-opioid receptor ligand is administered without the direct supervision of a health care professional (e.g., the compound is self-administered by the patient);

1.60 Any foregoing method, wherein the method does not comprise supervision or observation of the patient by a health care professional during or after (e.g., within 2 hours after) administration of a dose of the 5-HT$_{2A}$/mu-opioid receptor or 5-HT$_{2A}$/D1 and/or D2/mu-opioid receptor ligand;

1.61 Any foregoing method, wherein the method does not put the patient at risk for sedation, dissociation, abuse, misuse, or suicidal ideation;

1.62 Any foregoing method, wherein the method does not result in hypertension (e.g., systolic and/or diastolic hypertension) within four hours after administration of a dose of the 5-HT$_{2A}$/mu-opioid receptor or 5-HT$_{2A}$/D1 and/or D2/mu-opioid receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

1.63 Any foregoing method, wherein the method does not result in cognitive decline;

1.64 Any foregoing method, wherein the patient has (e.g., has been diagnosed with) or is at risk of aneurysmal vascular disease (e.g., thoracic aorta, abdominal aorta, intracranial, or peripheral arterial aneurysms), arteriovenous malformation or intracerebral hemorrhage;

1.65 Any foregoing method, wherein the patient is under concurrent treatment with an oral antidepressant selected from duloxetine, escitalopram, sertraline, or venlafaxine;

1.66 Any foregoing method, wherein the patient is not under concurrent treatment with an oral antidepressant selected from duloxetine, escitalopram, sertraline, or venlafaxine.

1.67 Any foregoing method, wherein the patient is unresponsive to, or cannot be treated with ketamine (e.g., S-ketamine), e.g., because it is contraindicated in said patient.

In another aspect, the disclosure provides a 5-HT$_{2A}$/mu-opioid receptor or 5-HT$_{2A}$/D1 and/or D2/mu-opioid receptor ligand, e.g. a compound of Formula I, as hereinbefore described, in free or salt form, optionally in deuterated form, for use in the acute treatment of depression or anxiety, e.g., for use in any of Methods 1, et seq.

In another aspect, the disclosure provides the use of a 5-HT$_{2A}$/mu-opioid receptor or 5-HT/D1 and/or D2/mu-opioid receptor ligand, e.g. a compound of Formula I, as hereinbefore described, in free or salt form, optionally in deuterated form, in in the manufacture of a medicament for the acute treatment of depression or anxiety, e.g., for any of Methods 1, et seq.

In a particular embodiment, the present disclosure provides a method (Method 2) for the enhancing mTOR (e.g., mTORC1) signaling, e.g., in the brain (e.g., in the hippocampus, or in the prefrontal cortex, or in the mPFC) comprising administering to a patient in need thereof, a therapeutically effective amount of a 5-HT$_{2A}$/mu-opioid receptor or 5-HT$_{2A}$/D1 and/or D2/mu-opioid receptor ligand, for example, a compound of Formula I:

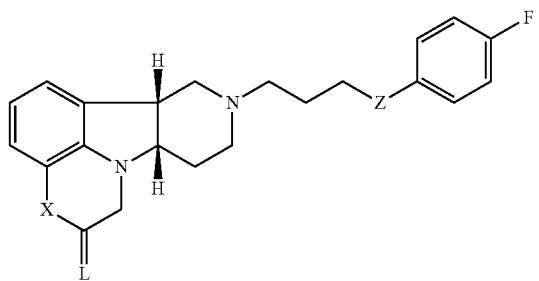

wherein:

X is —N(H)—, —N(CH$_3$)— or —O—;

L is selected from O, NH, NR$^a$, and S

Z is —O—;

R$_a$ is H or C$_{1-4}$alkyl;

optionally in deuterated form, in free, pharmaceutically acceptable salt or prodrug form. For example, Method 2 may be as follows:

2.1. Method 2, wherein X in the compound of Formula I is —N(H)—, —N(CH$_3$)— or —O—;

2.2. Method 2 or 2.1, wherein X in the compound of Formula I is —N(H);

2.3. Method 2 or 2.1, wherein X in the compound of Formula I is —N(CH$_3$)—;

2.4. Method 2 or 2.1, wherein X in the compound of Formula I is —O—;

2.5. Method 2 or any of formulae 2.1-2.4, wherein L in the compound of Formula I is O;

2.6. Method 2 or any of formulae 2.1-2.4, wherein L in the compound of Formula I is NH or NR$^a$;

2.7. Method 2 or any of formulae 2.1-2.4, wherein L in the compound of Formula I is S;

2.8. Method 2 or any of formulae 2.1-2.4, wherein the compound is:

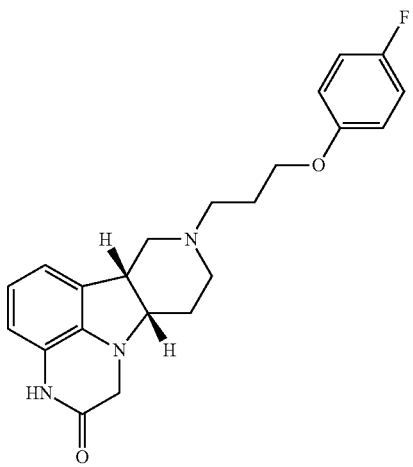 [SMILES: O=C1CN2c3c(cccc3[C@@H]3CN(CCCOc4ccc(F)cc4)CC[C@@H]32)N1]

2.9. Any of Method 2 or 2.1-2.8, wherein the Compound of Formula I is in the form of the tosylate salt;

2.10. Any of Method 2 or 2.1-2.9, wherein the Compound of Formula I is in the form of the free base;

2.11. Method 2 or any of 2.1-2.10 wherein the Compound of Formula I is in deuterated form, e.g., wherein the deuterium:protium ratio for a specified carbon-bound hydrogen atom is significantly higher, e.g., at least 2λ, for example at least 10× higher, than the natural isotope ratios;

2.12. Method 2.11, wherein the Compound of Formula I is:

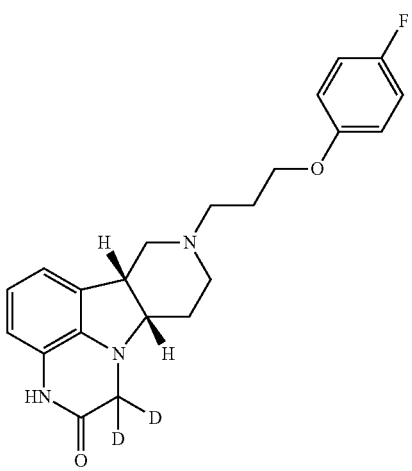

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free or pharmaceutically acceptable salt form, e.g. tosylate salt form;

2.13. Any foregoing method, wherein the 5-HT$_{2A}$/mu-opioid receptor or 5-HT$_{2A}$/D1 and/or D2/mu-opioid receptor ligand is a compound of Formula I in tosylate salt form, administered in a daily dose equivalent to 1 to 100 mg of free base, e.g., 1 to 75 mg, or 1 to 60 mg, or 1 to 40 mg, or 1 to 20 mg, or 1 to 10 mg, of free base;

2.14. Method 2.13 wherein the method comprises once daily administration of a unit dosage for oral administration, for example a tablet or capsule, comprising the compound of Formula I in tosylate salt form in an amount equivalent to 1 to 100 mg of free base, e.g., 1 to 75 mg, or 1 to 60 mg, or 1 to 40 mg, or 1 to 20 mg, or 1 to 10 mg, of free base, and a pharmaceutically acceptable diluent or carrier;

2.15. Method 2.13 wherein the method comprises once daily administration of a unit dosage for subcutaneous or transmucosal administration, e.g., a sublingual or buccal orally disintegrating tablet or film, comprising the compound of Formula I in tosylate salt form in an amount equivalent to 0.5 to 30 mg of free base, e.g., 1-10 mg of free base, and a pharmaceutically acceptable diluent or carrier;

2.16. Any foregoing method wherein the mTOR (e.g., mTORC1) signaling is increased within one week, e.g., within three days, e.g., within one day;

2.17. Any foregoing method wherein the patient is diagnosed as having suicidal ideation and/or suicidal tendencies;

2.18. Any foregoing method wherein the patient is diagnosed with acute anxiety (e.g., a short-duration anxious episode associated with generalized anxiety disorder, panic disorder, specific phobias, or social anxiety disorder, or social avoidance);

2.19. Any foregoing method wherein the patient is diagnosed with acute depression (e.g., acute major depressive episode, acute short-duration depressive episode, acute recurrent brief depressive episode);

2.20. Any foregoing method wherein the patient is diagnosed with treatment resistant depression (e.g., depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);

2.21. Any foregoing method wherein the patient is diagnosed with bipolar depression or major depressive disorder;

2.22. Any foregoing method wherein the 5-HT$_{2A}$/mu-opioid receptor or 5-HT$_{2A}$/D1 and/or D2/mu-opioid receptor ligand in combination (e.g. a fixed combination in a unit dosage form, or a free combination administered sequentially or simultaneously or within a 24 hour period) with an effective amount of an addition anxiolytic or antidepressant agent;

2.23. Method 2.22 wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:
(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
(c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

2.24. Any foregoing method wherein the method also reduces neuroinflammation (e.g., by suppressing pro-inflammatory cytokine expression [IL-1β, IL-6, TNF-α, CCL2] and/or by enhancing anti-inflammatory cytokine expression [IL-4, IL-10]);

2.25. Method 2.24, wherein the neuroinflammation is caused by an infectious agent, e.g., a gram-negative bacterium (e.g., meningococcal meningitis);

2.26. Any foregoing method, wherein the compound of Formula I is administered intra-nasally, subcutaneously, intravenously, orally, or sub-lingually, or intra-peritoneally, or buccally;

2.27. Any foregoing method, wherein the 5-HT$_{2A}$/mu-opioid receptor or 5-HT$_{2A}$/D1 and/or D2/mu-opioid receptor ligand is administered to the patient concurrently with a PDE1 (cyclic nucleoside phosphodiesterase 1) inhibitor (e.g., administered simultaneously, separately or sequentially), in free or pharmaceutically acceptable salt form;

2.28. Method 2.27, wherein the PDE1 inhibitor is a compound according to Formula II:

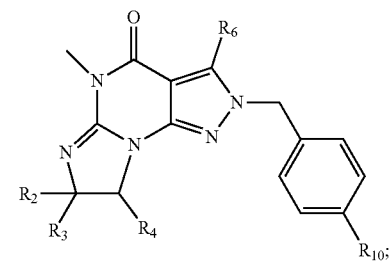

2.29. Method 2.27, wherein, in the Compound of Formula II, R$_6$ is phenylamino or 4-fluorophenylamino;

2.30. Method 2.27, wherein, in the Compound of Formula II, R$_{10}$ is 3-fluoropyrid-2-yl or methylcarbonyl;

2.31. Method 2.27, wherein, in the Compound of Formula II, R$_6$ is phenylamino or 4-fluorophenylamino and R$_{10}$ is 3-fluoropyrid-2-yl or methylcarbonyl;

2.32. Any Methods 2.27-2.31, wherein the Compound of Formula II is

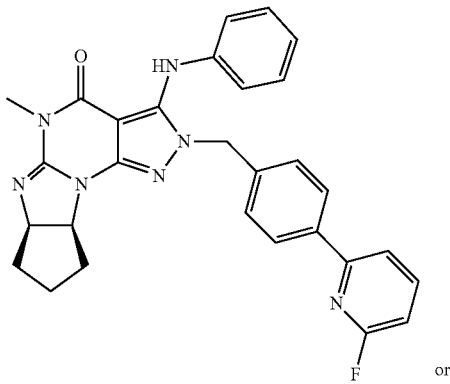

or

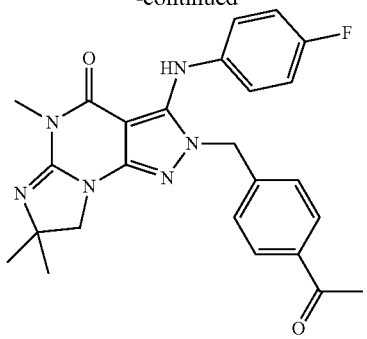

in free or pharmaceutically acceptable salt form.

2.33 Method 2.32, wherein the Compound of Formula II is in the form of the monophosphate salt;

2.34 Any of Methods 2.27-2.33, wherein the Compound of Formula I is:

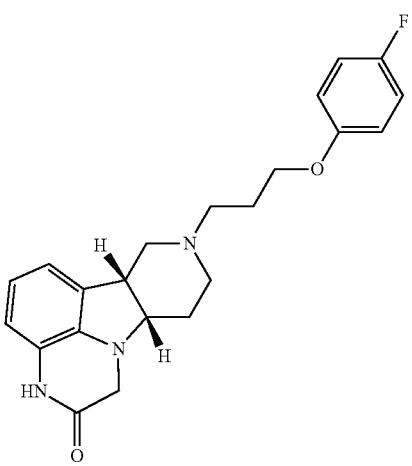 [SMILES: O=C1CN2c3c(cccc3[C@@H]3CN(CCCOc4ccc(F)cc4)CC[C@@H]32)N1]

in free or pharmaceutically acceptable salt form, e.g., tosylate salt form; and the Compound of Formula II is:

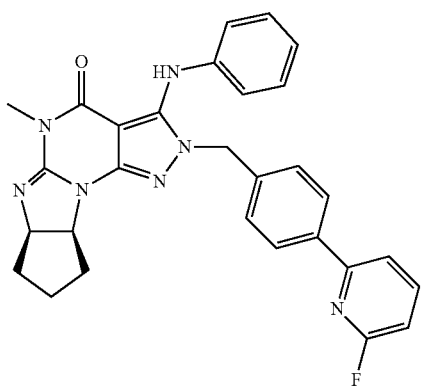 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, e.g., monophosphate salt form;

2.35 Any of Methods 2.27-2.34, comprising administration of a pharmaceutical composition comprising effective amounts of both a Compound of Formula I and a Compound of Formula II;

2.36 Any foregoing method, wherein the method further comprises the concurrent administration of another anti-depressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, a serotonin receptor antagonist, or any combination thereof), e.g., administered simultaneously, separately or sequentially;

2.37 Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

2.38 Any foregoing method, wherein the method further comprises the concurrent administration of a NMDA receptor allosteric modulator, e.g., a NMDA receptor glycine-site modulator, such as rapastinel, nebostinel, apimostinel, D-cycloserine or any combination thereof, e.g., administered simultaneously, separately or sequentially;

2.39 Any foregoing method, wherein the method provides the patient with an acute response (e.g., an acute enhancement in mTOR (e.g., mTORC1) signaling) to treatment with the therapeutic agent or agents (e.g., the Compound of Formula I, or the combination of the Compound or Formula I and the Compound of Formula II, and any additional antidepressant agents);

2.40 Method 2.39, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours);

2.41 Any foregoing method, wherein the 5-$HT_{2A}$/mu-opioid receptor or 5-$HT_{2A}$/D1 and/or D2/mu-opioid receptor ligand has an $IC_{50}$ of less than 250 nM or an $EC_{50}$ of less than 250 nM for activity (agonism and/or antagonism) at the 5-$HT_{2A}$ receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.42 Any foregoing method, wherein the 5-$HT_{2A}$/mu-opioid receptor or 5-$HT_{2A}$/D1 and/or D2/mu-opioid receptor ligand has an $IC_{50}$ of less than 250 nM or an $EC_{50}$ of less than 250 nM for activity (agonism and/or antagonism) at the mu-opioid receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.43 Any foregoing method, wherein the 5-$HT_{2A}$/D1 and/or D2/mu-opioid receptor ligand has an $IC_{50}$ of less than 250 nM or an $EC_{50}$ of less than 250 nM for activity (agonism and/or antagonism) at the D1 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.44 Any foregoing method, wherein the 5-$HT_{2A}$/D1 and/or D2/mu-opioid receptor ligand has an $IC_{50}$ of less than 250 nM or an $EC_{50}$ of less than 250 nM for activity (agonism and/or antagonism) at the D2 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.45 Any foregoing method, wherein the 5-$HT_{2A}$/mu-opioid receptor or 5-$HT_{2A}$/D1 and/or D2/mu-opioid receptor ligand has an $IC_{50}$ of less than 250 nM or an $EC_{50}$ of less than 250 nM for activity (agonism and/or antagonism) at the serotonin transporter (SERT), e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

2.46 Any foregoing method, wherein the 5-$HT_{2A}$/mu-opioid receptor or 5-$HT_{2A}$/D1 and/or D2/mu-opioid receptor ligand is a biased ligand at the mu-opioid receptor;

2.47 Any foregoing method, wherein the 5-$HT_{2A}$/mu-opioid receptor or 5-$HT_{2A}$/D1 and/or D2/mu-opioid receptor ligand is a compound of Formula I, e.g., in tosylate salt form, administered in the form of a long-acting injectable (LAI) composition, e.g., for intramuscular or subcutaneous injection;

2.48 Method 2.47, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

2.49 Method 2.47 or 2.48, wherein the LAI composition comprises the compound of Formula I dissolved, dispersed, suspended, or encapsulated in a polymeric matrix;

2.50 Method 2.49, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

2.51 Method 2.50, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, poly (alkyl alpha-cyanoacrylate) such as poly(butyl cyanoacrylate) or poly(2-octyl cyanoacrylate), poly(ortho ester), polycarbonate, polyortho-carbonate, a polyamino acid, (for example poly-gamma.-L-alanine, poly-.gamma.-benzyl-L-glutamic acid or poly-y-methyl-L-glutamic acid), and/or hyaluronic acid ester;

2.52 Method 2.50, wherein the one or more polymers comprises polylactic acid, polyglycolic acid, polycitric acid, polymalic acid, or a poly(lactic acid-glycolic acid) copolymer;

2.53 Method 2.50, wherein the one or more polymers comprises a poly(lactic acid-glycolic acid) copolymer, e.g., poly-d,l-lactide-co-glycolide;

2.54 Any foregoing method, wherein the 5-HT$_{2A}$/mu-opioid receptor or 5-HT$_{2A}$/D1 and/or D2/mu-opioid receptor ligand is administered as monotherapy, e.g., it is not administered concurrently or in conjunction with an anti-depressant, anti-psychotic, or anti-anxiety agent;

2.55 Any foregoing method, wherein the 5-HT$_{2A}$/mu-opioid receptor or 5-HT$_{2A}$/D1 and/or D2/mu-opioid receptor ligand is administered without the direct supervision of a health care professional (e.g., the compound is self-administered by the patient);

2.56 Any foregoing method, wherein the method does not comprise supervision or observation of the patient by a health care professional during or after (e.g., within 2 hours after) administration of a dose of the 5-HT$_{2A}$/mu-opioid receptor or 5-HT$_{2A}$/D1 and/or D2/mu-opioid receptor ligand;

2.57 Any foregoing method, wherein the method does not put the patient at risk for sedation, dissociation, abuse, misuse, or suicidal ideation;

2.58 Any foregoing method, wherein the method does not result in hypertension (e.g., systolic and/or diastolic hypertension) within four hours after administration of a dose of the 5-HT$_{2A}$/mu-opioid receptor or 5-HT$_{2A}$/D1 and/or D2/mu-opioid receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

2.59 Any foregoing method, wherein the method does not result in cognitive decline;

2.60 Any foregoing method, wherein the patient has (e.g., has been diagnosed with) or is at risk of aneurysmal vascular disease (e.g., thoracic aorta, abdominal aorta, intracranial, or peripheral arterial aneurysms), arteriovenous malformation or intracerebral hemorrhage;

2.61 Any foregoing method, wherein the patient is under concurrent treatment with an oral antidepressant selected from duloxetine, escitalopram, sertraline, or venlafaxine;

2.62 Any foregoing method, wherein the patient is not under concurrent treatment with an oral antidepressant selected from duloxetine, escitalopram, sertraline, or venlafaxine.

2.63 Any foregoing method, wherein the patient is unresponsive to, or cannot be treated with ketamine (e.g., S-ketamine), e.g., because it is contraindicated in said patient.

In another aspect, the disclosure provides a 5-HT$_{2A}$/mu-opioid receptor or 5-HT$_{2A}$/D1 and/or D2/mu-opioid receptor ligand, e.g. a compound of Formula I, as hereinbefore described, in free or salt form, optionally in deuterated form, for use in the enhancement of mTOR (e.g., mTORC1) signaling, e.g., in the brain (e.g., in the hippocampus, or in the prefrontal cortex, or in the mPC), e.g., for use in any of Methods 2, et seq.

In another aspect, the disclosure provides the use of a 5-HT$_{2A}$/mu-opioid receptor or 5-HT$_{2A}$/D1 and/or D2/mu-opioid receptor ligand, e.g. a compound of Formula I, as hereinbefore described, in free or salt form, optionally in deuterated form, in in the manufacture of a medicament for the enhancement of mTOR (e.g., mTORC1) signaling, e.g., in the brain (e.g., in the hippocampus, or in the prefrontal cortex, or in the mPFC), e.g., for any of Methods 2, et seq.

In a particular embodiment, the present disclosure provides a method (Method 3) for reducing neuroinflammation, e.g., in the brain (e.g., in the prefrontal cortex, or in the mPFC) comprising administering to a patient in need thereof, a therapeutically effective amount of a 5-HT$_{2A}$/mu-opioid receptor or 5-HT$_{2A}$/D1 and/or D2/mu-opioid receptor ligand, for example, a compound of Formula I:

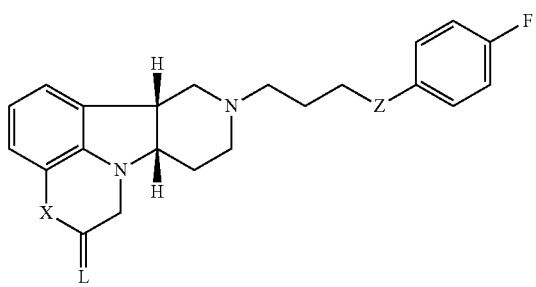

wherein:

X is —N(H)—, —N(CH$_3$)— or —O—;

L is selected from O, NH, NR$^a$, and S

Z is —O—;

R$_a$ is H or C$_{1-4}$alkyl;

optionally in deuterated form, in free, pharmaceutically acceptable salt or prodrug form. For example, Method 3 may be as follows:

3.1. Method 3, wherein X in the compound of Formula I is —N(H)—, —N(CH$_3$)— or —O—;

3.2. Method 3 or 3.1, wherein X in the compound of Formula I is —N(H);

3.3. Method 3 or 3.1, wherein X in the compound of Formula I is —N(CH$_3$)—;

3.4. Method 3 or 3.1, wherein X in the compound of Formula I is —O—;

3.5. Method 3 or any of formulae 1.1-3.4, wherein L in the compound of Formula I is O;

3.6. Method 3 or any of formulae 3.1-3.4, wherein L in the compound of Formula I is NH or NR$^a$;

3.7. Method 3 or any of formulae 3.1-3.4, wherein L in the compound of Formula I is S;

3.8. Method 3 or any of formulae 3.1-3.4, wherein the compound is:

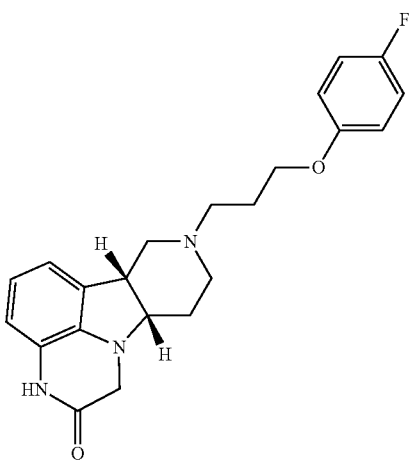 [SMILES: O=C1CN2c3c(cccc3[C@@H]3CN(CCCOc4ccc(F)cc4)CC[C@@H]32)N1]

3.9. Any of Method 3 or 3.1-3.8, wherein the Compound of Formula I is in the form of the tosylate salt;
3.10. Any of Method 3 or 3.1-3.9, wherein the Compound of Formula I is in the form of the free base;
3.11. Method 3 or any of 3.1-3.10 wherein the Compound of Formula I is in deuterated form, e.g., wherein the deuterium:protium ratio for a specified carbon-bound hydrogen atom is significantly higher, e.g., at least 2λ, for example at least 10× higher, than the natural isotope ratios;
3.12. Method 3.11, wherein the Compound of Formula I is:

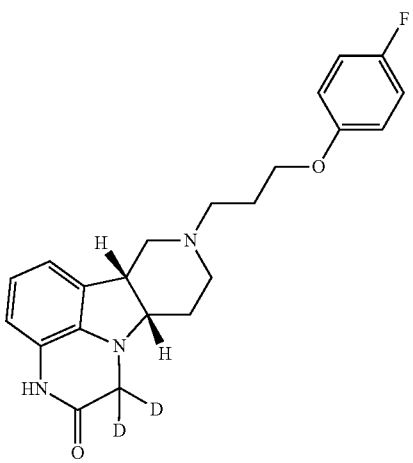

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free or pharmaceutically acceptable salt form, e.g. tosylate salt form;
3.13. Any foregoing method, wherein the 5-HT$_{2A}$/mu-opioid receptor or 5-HT$_{2A}$/D1 and/or D2/mu-opioid receptor ligand is a compound of Formula I in tosylate salt form, administered in a daily dose equivalent to 1 to 100 mg of free base, e.g., 1 to 75 mg, or 1 to 60 mg, or 1 to 40 mg, or 1 to 20 mg, or 1 to 10 mg, of free base;
3.14. Method 3.13 wherein the method comprises once daily administration of a unit dosage for oral administration, for example a tablet or capsule, comprising the compound of Formula I in tosylate salt form in an amount equivalent to 1 to 100 mg of free base, e.g., 1 to 75 mg, or 1 to 60 mg, or 1 to 40 mg, or 1 to 20 mg, or 1 to 10 mg, of free base, and a pharmaceutically acceptable diluent or carrier;
3.15. Method 3.13 wherein the method comprises once daily administration of a unit dosage for subcutaneous or transmucosal administration, e.g., a sublingual or buccal orally disintegrating tablet or film, comprising the compound of Formula I in tosylate salt form in an amount equivalent to 0.5 to 30 mg of free base, e.g., 1-10 mg of free base, and a pharmaceutically acceptable diluent or carrier;
3.16. Any foregoing method wherein the neuroinflammation is reduced within one week, e.g., within three days, e.g., within one day;
3.17. Any foregoing method wherein the patient is diagnosed as having suicidal ideation and/or suicidal tendencies;
3.18. Any foregoing method wherein the patient is diagnosed with acute anxiety (e.g., a short-duration anxious episode associated with generalized anxiety disorder, panic disorder, specific phobias, or social anxiety disorder, or social avoidance);
3.19. Any foregoing method wherein the patient is diagnosed with acute depression (e.g., acute major depressive episode, acute short-duration depressive episode, acute recurrent brief depressive episode);
3.20. Any foregoing method wherein the patient is diagnosed with treatment resistant depression (e.g., depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);
3.21. Any foregoing method wherein the patient is diagnosed with bipolar depression or major depressive disorder;
3.22. Any foregoing method wherein the 5-HT$_{2A}$/mu-opioid receptor or 5-HT$_{2A}$/D1 and/or D2/mu-opioid receptor ligand in combination (e.g. a fixed combination in a unit dosage form, or a free combination administered sequentially or simultaneously or within a 24 hour period) with an effective amount of an addition anxiolytic or antidepressant agent;
3.23. Method 3.22 wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:
(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);

(b) Serotonin-norepinephrine reuptake inhibitors (SN-RIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);

(c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);

(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

3.24. Any foregoing method, wherein the method also enhances mTOR (e.g., mTORC1) signaling (e.g., in brain tissue, or in the hippocampus, or in the pre-frontal cortex, or in the mPFC);

3.25. Any foregoing method wherein the method reduces neuroinflammation by suppressing pro-inflammatory cytokine expression [IL-1β, IL-6, TNF-α, CCL2], and/or by enhancing anti-inflammatory cytokine expression [IL-4, IL-10];

3.26. Any foregoing method, wherein the neuroinflammation is caused by or associated with any one or more of the following: an infectious agent, e.g., a gram-negative bacterium (e.g., meningococcal meningitis); a neurodegenerative condition, e.g., Alzheimer's disease, Parkinson's disease, amyotrophic lateral sclerosis, multiple sclerosis, or prion disease; intracerebral hemorrhage or intracerebral hypoxia; traumatic brain injury; and chemotherapy; conditions causing increased intracerebral levels of pro-inflammatory cytokines (e.g., IL-1β, IL-6, TNF-α, CCL2) and/or causing decreased levels of anti-inflammatory cytokines (e.g., IL-4 IL-10), or combinations thereof;

3.27. Any foregoing method, wherein the compound of Formula I is administered intra-nasally, subcutaneously, intravenously, orally, or sub-lingually, or intra-peritoneally, or buccally;

3.28. Any foregoing method, wherein the 5-HT$_{2A}$/mu-opioid receptor or 5-HT$_{2A}$/D1 and/or D2/mu-opioid receptor ligand is administered to the patient concurrently with a PDE1 (cyclic nucleoside phosphodiesterase 1) inhibitor (e.g., administered simultaneously, separately or sequentially), in free or pharmaceutically acceptable salt form;

3.29. Method 3.28, wherein the PDE1 inhibitor is a compound according to Formula II:

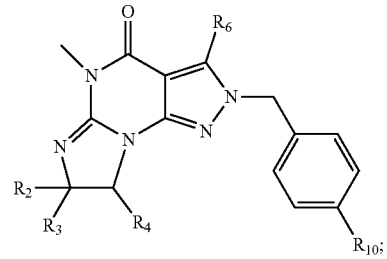

3.30. Method 3.29, wherein, in the Compound of Formula II, $R_6$ is phenylamino or 4-fluorophenylamino;

3.31. Method 3.29, wherein, in the Compound of Formula II, $R_{10}$ is 3-fluoropyrid-2-yl or methylcarbonyl;

3.32. Method 3.29, wherein, in the Compound of Formula II, $R_6$ is phenylamino or 4-fluorophenylamino and $R_{10}$ is 3-fluoropyrid-2-yl or methylcarbonyl;

3.33. Any Methods 3.29-3.32, wherein the Compound of Formula II is

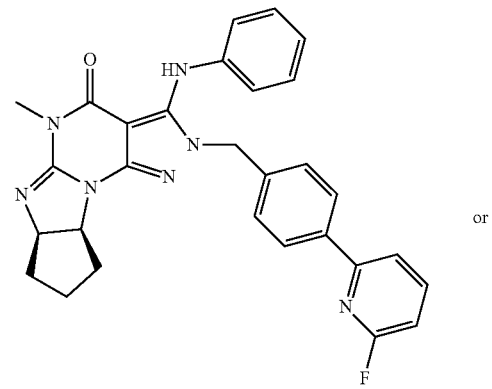

or

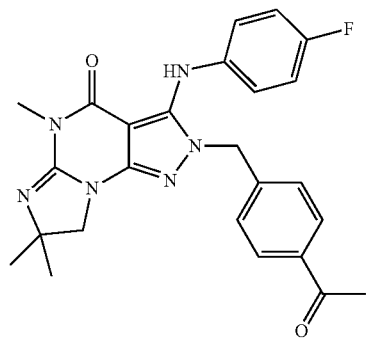

in free or pharmaceutically acceptable salt form.

3.34 Method 3.33, wherein the Compound of Formula II is in the form of the monophosphate salt;

3.35 Any of Methods 3.29-3.34, wherein the Compound of Formula I is:

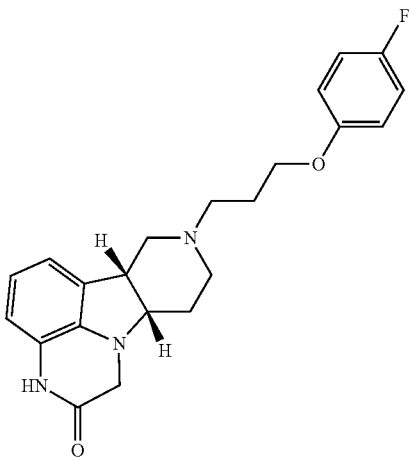 [SMILES: O=C1CN2c3c(cccc3[C@@H]3CN(CCCOc4ccc(F)cc4)CC[C@@H]32)N1]

in free or pharmaceutically acceptable salt form, e.g., tosylate salt form; and the Compound of Formula II is:

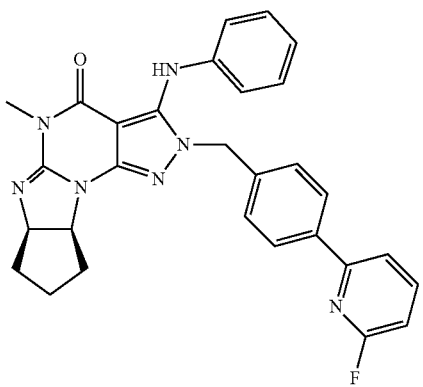 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, e.g., monophosphate salt form;

3.36 Any of Methods 3.29-3.35, comprising administration of a pharmaceutical composition comprising effective amounts of both a Compound of Formula I and a Compound of Formula II;

3.37 Any foregoing method, wherein the method further comprises the concurrent administration of another anti-depressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, a serotonin receptor antagonist, or any combination thereof), e.g., administered simultaneously, separately or sequentially;

3.38 Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

3.39 Any foregoing method, wherein the method further comprises the concurrent administration of a NMDA receptor allosteric modulator, e.g., a NMDA receptor glycine-site modulator, such as rapastinel, nebostinel, apimostinel, D-cycloserine or any combination thereof, e.g., administered simultaneously, separately or sequentially;

3.40 Any foregoing method, wherein the method provides the patient with an acute response (e.g., an acute reduction in neuroinflammation) to treatment with the therapeutic agent or agents (e.g., the Compound of Formula I, or the combination of the Compound or Formula I and the Compound of Formula II, and any additional antidepressant agents);

3.41 Method 3.40, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours);

3.42 Any foregoing method, wherein the 5-HT$_{2A}$/mu-opioid receptor or 5-HT$_{2A}$/D1 and/or D2/mu-opioid receptor ligand has an IC$_{50}$ of less than 250 nM or an EC$_{50}$ of less than 250 nM for activity (agonism and/or antagonism) at the 5-HT$_{2A}$ receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.43 Any foregoing method, wherein the 5-HT$_{2A}$/mu-opioid receptor or 5-HT$_{2A}$/D1 and/or D2/mu-opioid receptor ligand has an IC$_{50}$ of less than 250 nM or an EC$_{50}$ of less than 250 nM for activity (agonism and/or antagonism) at the mu-opioid receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.44 Any foregoing method, wherein the 5-HT$_{2A}$/D1 and/or D2/mu-opioid receptor ligand has an IC$_{50}$ of less than 250 nM or an EC$_{50}$ of less than 250 nM for activity (agonism and/or antagonism) at the D1 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.45 Any foregoing method, wherein the 5-HT$_{2A}$/D1 and/or D2/mu-opioid receptor ligand has an IC$_{50}$ of less than 250 nM or an EC$_{50}$ of less than 250 nM for activity (agonism and/or antagonism) at the D2 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.46 Any foregoing method, wherein the 5-HT$_{2A}$/mu-opioid receptor or 5-HT$_{2A}$/D1 and/or D2/mu-opioid receptor ligand has an IC$_{50}$ of less than 250 nM or an EC$_{50}$ of less than 250 nM for activity (agonism and/or antagonism) at the serotonin transporter (SERT), e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

3.47 Any foregoing method, wherein the 5-HT$_{2A}$/mu-opioid receptor or 5-HT$_{2A}$/D1 and/or D2/mu-opioid receptor ligand is a biased ligand at the mu-opioid receptor;

3.48 Any foregoing method, wherein the 5-HT$_{2A}$/mu-opioid receptor or 5-HT$_{2A}$/D1 and/or D2/mu-opioid receptor ligand is a compound of Formula I, e.g., in tosylate salt form, administered in the form of a long-acting injectable (LAI) composition, e.g., for intramuscular or subcutaneous injection;

3.49 Method 3.48, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

3.50 Method 3.48 or 3.49, wherein the LAI composition comprises the compound of Formula I dissolved, dispersed, suspended, or encapsulated in a polymeric matrix;

3.51 Method 3.50, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

3.52 Method 3.51, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, poly (alkyl alpha-cyanoacrylate) such as poly(butyl cyanoacrylate) or poly(2-octyl cyanoacrylate), poly(ortho ester), polycarbonate, polyortho-carbonate, a polyamino acid, (for example poly-gamma.-L-alanine, poly-.gamma.-benzyl-L-glutamic acid or poly-y-methyl-L-glutamic acid), and/or hyaluronic acid ester;

3.53 Method 3.51, wherein the one or more polymers comprises polylactic acid, polyglycolic acid, polycitric acid, polymalic acid, or a poly(lactic acid-glycolic acid) copolymer;

3.54 Method 3.51, wherein the one or more polymers comprises a poly(lactic acid-glycolic acid) copolymer, e.g., poly-d,l-lactide-co-glycolide;

3.55 Any foregoing method, wherein the 5-HT$_{2A}$/mu-opioid receptor or 5-HT$_{2A}$/D1 and/or D2/mu-opioid receptor ligand is administered as monotherapy, e.g., it is not administered concurrently or in conjunction with an anti-depressant, anti-psychotic, or anti-anxiety agent;

3.56 Any foregoing method, wherein the 5-HT$_{2A}$/mu-opioid receptor or 5-HT$_{2A}$/D1 and/or D2/mu-opioid receptor ligand is administered without the direct supervision of a health care professional (e.g., the compound is self-administered by the patient);

3.57 Any foregoing method, wherein the method does not comprise supervision or observation of the patient by a health care professional during or after (e.g., within 2 hours after) administration of a dose of the 5-HT$_{2A}$/mu-opioid receptor or 5-HT$_{2A}$/D1 and/or D2/mu-opioid receptor ligand;

3.58 Any foregoing method, wherein the method does not put the patient at risk for sedation, dissociation, abuse, misuse, or suicidal ideation;

3.59 Any foregoing method, wherein the method does not result in hypertension (e.g., systolic and/or diastolic hypertension) within four hours after administration of a dose of the 5-HT$_{2A}$/mu-opioid receptor or 5-HT$_{2A}$/D1 and/or D2/mu-opioid receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

3.60 Any foregoing method, wherein the method does not result in cognitive decline;

3.61 Any foregoing method, wherein the patient has (e.g., has been diagnosed with) or is at risk of aneurysmal vascular disease (e.g., thoracic aorta, abdominal aorta, intracranial, or peripheral arterial aneurysms), arteriovenous malformation or intracerebral hemorrhage;

3.62 Any foregoing method, wherein the patient is under concurrent treatment with an oral antidepressant selected from duloxetine, escitalopram, sertraline, or venlafaxine;

3.63 Any foregoing method, wherein the patient is not under concurrent treatment with an oral antidepressant selected from duloxetine, escitalopram, sertraline, or venlafaxine.

3.64 Any foregoing method, wherein the patient is unresponsive to, or cannot be treated with ketamine (e.g., S-ketamine), e.g., because it is contraindicated in said patient.

In another aspect, the disclosure provides a 5-HT$_{2A}$/mu-opioid receptor or 5-HT$_{2A}$/D1 and/or D2/mu-opioid receptor ligand, e.g. a compound of Formula I, as hereinbefore described, in free or salt form, optionally in deuterated form, for use in the reduction of neuroinflammation, e.g., in the brain (e.g., in the hippocampus, or in the prefrontal cortex, or in the mPC), e.g., for use in any of Methods 3, et seq.

In another aspect, the disclosure provides the use of a 5-HT$_{2A}$/mu-opioid receptor or 5-HT$_{2A}$/D1 and/or D2/mu-opioid receptor ligand, e.g. a compound of Formula I, as hereinbefore described, in free or salt form, optionally in deuterated form, in in the manufacture of a medicament for the reduction of neuroinflammation, e.g., in the brain (e.g., in the hippocampus, or in the prefrontal cortex, or in the mPC), e.g., for any of Methods 3, et seq.

The term "5-HT$_{2A}$/mu-opioid receptor" ligand refers to a compound which displays, at least, pharmacological activity at both the serotonin 5-HT$_{2A}$ receptor and at the mu-opioid receptor, for example, compounds having an IC$_{50}$ of less than 250 nM or an EC$_{50}$ of less than 250 nM for activity (agonism and/or antagonism) at each of said receptors. In some embodiments, this term refers to a compound having an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at one or both of these receptors (agonism or antagonism).

The term "5-HT/D1 and/or D2/mu-opioid receptor ligand" refers to a compound which displays, at least, pharmacological activity at both the serotonin 5-HT$_{2A}$ receptor and at the mu-opioid receptor, and either the D1 or D2 receptor (or both), for example, compounds having an IC$_{50}$ of less than 250 nM or an EC$_{50}$ of less than 250 nM for activity (agonism and/or antagonism) at each of said receptors. In some embodiments, this term refers to a compound having an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at one or both of these receptors (agonism or antagonism).

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

The term "patient" may include a human or non-human patient.

The Diagnostic and Statistical Manual of Mental Disorders, 5th Edition ("DSM-5"), defines "major depressive disorder" (MDD) as having five or more of a set of symptoms during the same two-week period of time, which symptoms represent a change from the patient's previous functioning. The five symptoms are selected from depressed mood, markedly diminished interest or pleasure in almost all activities, significant weight changes, insomnia or hyposomnia, psychomotor agitation or retardation, fatigue, feelings of worthlessness or excessive guilt, diminished ability to think or indecisiveness, and recurrent thoughts of death or suicidal ideation, wherein each of such symptoms is present nearly every day. At a minimum, MDD diagnosis requires at least depressed mood or loss of interest or pleasure as one of the five symptoms. MDD may consist of one or more "major depressive episodes" which can be spaced many weeks or months apart (more than 2 weeks apart to qualify as separate episodes). The DSM-5 notes that there is a risk of suicidal behavior at all time during a major depressive episode.

By its nature, MDD is an acute disorder in so far as the DSM-5 distinguishes it from "persistent depressive disorder", in which a patient has many of the same symptoms as for MDD, but which persists for at least a 2-year period. In addition to MDD, the DSM-5 also defines a "short-duration depressive episode" as having a depressed affect and at least four of the other symptoms which define MDD for at least 4 days, but less than 14 days. The DSM further defines "recurrent brief depression" as the concurrent presence of depressed mood and at least four other symptoms of depression for 2 to 13 days at least once per month, and persisting for at least 12 consecutive months. Thus, recurrent brief depression similarly consists of brief episodes of depression which recur regularly.

The DSM-5 also includes major depressive episodes as one of the diagnostic criteria for a patient suffering from bipolar disorder. Thus, a patient presenting a major depressive episode may be suffering from either major depressive disorder or bipolar disorder.

It is apparent that there are is a particular need for effective treatment of depression during the earliest stages of a major depressive episode, since each day of such episode can have profound consequences for a patient, yet typical SSRI anti-depressive agents take up to 2-4 weeks for beneficial effects to appear. The same is true for treatment of short duration depressive episodes as well as individual episodes of recurrent brief depression.

The DSM-5 categorizes what has traditionally been termed "post partum depression" or "peri-partum depression" as a merely a sub-type of the DSM's recognized depressive disorders, rather than as an independent depressive disorder. Thus, both major depressive disorder and acute depressive disorders can be diagnosed as being "with peripartum onset" (DSM-5 also does not distinguish peri- versus post-partum). Thus, as used herein, any of the depression indications may be considered to include such depression indication with peri-partum or post-partum onset, and thus, these indications embrace post-partum and peri-partum depression as well.

Thus, as used herein, the term "acute depression" refers to the initial period of what may be a brief or a chronic episode of depression (e.g., lasting 2 days to 2 weeks, or 2 weeks to 2 months, or 2 months to 2 years, or more). "Acute depression" may thus refer to the initial period of a major depressive episode, a short-duration depressive episode, or a recurrent brief depressive episode. There is a particular need in the art for the treatment of such acute stages of depressive episodes. A treatment initiated during this acute phase of depression may be continued indefinitely in those patients which respond thereto.

The DSM-5 defines a variety of anxiety disorders, including generalized anxiety disorder, panic disorder, social anxiety disorder, and specific phobias Like the depressive disorders discussed above, anxiety disorders can be marked by recurrent episodes of short duration, such as panic attacks, which may persist over the course of a chronic disorder. For example, generalized anxiety disorder is defined by the DSM-5 to require excessive anxiety and worry occurring more days that not for at least 6 months, about a number of events or activities. A panic attack is defined as an abrupt surge of intense fear or intense discomfort that reaches a peak within minutes, but it can repeatedly recur in response to either expected stimuli or unexpected stimuli. Thus, as for the depressive disorders described above, there is a need for rapidly-acting anxiolytic agents that can treat the symptoms of anxiety or panic, yet some of the most common treatments for anxiety disorders are the SSRIs and other antidepressant agents which take 2-4 weeks to provide relief.

As used herein, "acute anxiety" refers to any short-duration episode of anxiety, e.g., lasting from one day or less to one week, which may be part of a chronic course of anxiety (e.g., lasting 2 days to 2 weeks, or 2 weeks to 2 months, or 2 months to 2 years, or more). "Acute anxiety" may thus include a panic attack or any specific instance of an anxious response to triggering stimuli or events (e.g., to the stimuli which trigger a specific phobia, the events which trigger social anxiety or generalized anxiety). There is a particular need in the art for the treatment of such acute stages of anxious episodes. A treatment initiated during this acute phase of anxiety may be continued indefinitely in those patients which respond thereto.

Social avoidance can be a critical and debilitating symptom in patients suffering from anxiety disorders, especially social anxiety disorder, as well as in patients suffering from traumatic anxiety disorders. Social avoidance is often one of the key determinants of whether a person with a severe anxiety disorder is capable of maintaining familial relationships or employment relationships. It has been unexpectedly found that certain substituted fused gamma carbolines having $5-HT_{2A}$ and dopamine receptor activity, such as the compound of Formula A (lumateperone), are effective in treating the emotional experience symptoms of psychiatric disorders (e.g., the emotional experience negative symptoms of schizophrenics). Negative symptoms of schizophrenia can be divided into two categories: emotional experience (e.g., emotional withdrawal, passive social withdrawal, active social avoidance) and emotional expression (e.g., blunted effect, poor rapport, lack of spontaneity, and motor retardation). In two clinical studies of patients with acute exacerbated schizophrenia, administration of lumateperone once daily (60 mg P.O.), for up to 28 days, resulted in a significant and unexpected improvement in symptoms of emotional experience compared to placebo. These are the symptoms that are most highly correlated with interpersonal functioning. As such, such compounds, including the compounds of Formula I, may be highly effective in treating the emotional experience symptoms of other psychiatric disorders, such as social anxiety disorders, or any other psychiatric disorders in which social withdrawal and social avoidance are symptoms.

If not otherwise specified or clear from context, the following terms herein have the following meanings:

"Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$ alkoxy (e.g., ethoxy) groups. In another embodiment, alkyl contains 1 to 21 carbon atoms, preferably straight chain and optionally saturated or unsaturated, for example $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The 5-$HT_{2A}$/mu-opioid receptor or 5-$HT_{2A}$/D1 and/or D2/mu-opioid receptor ligand, for example a substituted heterocycle fused gamma-carbolines as described herein may be in free, pharmaceutically acceptable salt or prodrug form. Pharmaceutically acceptable salts of such compounds (e.g., Compound of Formula I) or of Compounds of Formula II include, for example, acid addition salts formed using any of the following acids: hydrochloric, hydrobromic, sulfuric, sulfamic, phosphoric, nitric, acetic, propionic, succinic, glycolic, stearic, lactic, malic, tartaric, citric, ascorbic, maleic, phenylacetic, glutamic, benzoic, salicylic, sulfanilic, fumaric, toluenesulfonic, methanesulfonic, ethanedisulfonic, oxalic, and isethionic. Where dosages or amounts of a salt are given by weight, e.g., milligrams per day or milligrams per unit dose, the dosage amount of the salt is given as the weight of the corresponding free base, unless otherwise indicated.

In any and all embodiments described herein, the 5-$HT_{2A}$/mu-opioid receptor or 5-$HT_{2A}$/D1 and/or D2/mu-opioid receptor ligand may also be a SERT ligand, i.e., said compounds may be a 5-$HT_{2A}$/SERT or a 5-$HT_{2A}$/D1 and/or D2/SERT receptor ligand.

The term "concurrently" when referring to a therapeutic use means administration of two or more active ingredients to a patient as part of a regimen for the treatment of a disease or disorder, whether the two or more active agents are given at the same or different times or whether given by the same or different routes of administrations. Concurrent administration of the two or more active ingredients may be at different times on the same day, or on different dates or at different frequencies.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

With respect to concurrent treatment using a 5-$HT_{2A}$/mu-opioid receptor or 5-$HT_{2A}$/D1 and/or D2/mu-opioid receptor ligand (e.g., a compound of Formula I) and an NMDA receptor antagonist (e.g., ketamine), without being bound by theory, it is believed that the combination of these agents would permit lower doses of both agents to be used to treat depression, or other neuropsychiatric disorders described herein, such that the dissociative effects produced by the NMDA receptor antagonist would be minimized while the synergistic antidepressants effects would be maximized.

Dosages employed in practicing the present disclosure will of course vary depending, e.g. on the particular disease or condition to be treated, the particular active compounds used, the mode of administration, and the therapy desired. Unless otherwise indicated, an amount of an active compound for administration (whether administered as a free base or as a salt form) refers to or is based on the amount of the compound in free form (i.e., the calculation of the amount is based on the amount of active moiety in free form, not taking into account the weight of the counter ion in the case of a salt). The 5-$HT_{2A}$/mu-opioid receptor or 5-$HT_{2A}$/D1 and/or D2/mu-opioid receptor ligand may be administered by any suitable route, including orally, intra-muscularly, subcutaneously, parenterally or transdermally, but are preferably administered orally. The 5-$HT_{2A}$/mu-opioid receptor or 5-$HT_{2A}$/D1 and/or D2/mu-opioid receptor ligand may be administered by any suitable route, including oral, parenteral, transdermal, or transmucosal, for example in the form of a tablet, a capsule, a subcutaneous injection, or an oral, rapidly disintegrating tablet or film for sublingual or buccal administration.

For the avoidance of doubt, any disclosure of a numerical range, e.g., "up to X" amount is intended to include the upper numerical limit X. Therefore, a disclosure of "up to 60 mg" is intended to include 60 mg.

Pharmaceutical compositions comprising compounds of the Disclosure may be prepared using conventional diluents or excipients and techniques known in the galenic art. Thus, oral dosage forms may include tablets, capsules, solutions, suspensions and the like.

Compounds of the present disclosure may be included as a depot formulation, e.g., by dispersing, dissolving, suspending, or encapsulating the Compounds of the Invention in a polymeric matrix as described in herein, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 1 week to 3 months.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer, such as PLGA 50:50, PLGA 85:15 and PLGA 90:10

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity Example 1: Synthesis of (6bR,10aS)-8-(3-(4-fluorophenoxy)propyl)-6b,7,8,9,10,10a-hexahydro-1H-pyrido[3',4':4,5]pyrrolo[1,2,3-de]quinoxalin-2(3H)-one

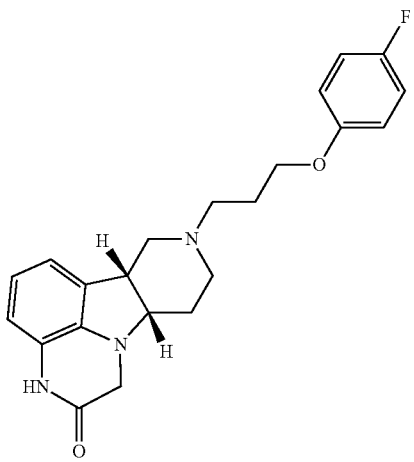 [SMILES: O=C1CN2c3c(cccc3[C@@H]3CN(CCCOc4ccc(F)cc4)CC[C@@H]32)N1]

A mixture of (6bR,10aS)-6b,7,8,9,10,10a-hexahydro-1H-pyrido[3',4':4,5]pyrrolo[1,2,3-de]quinoxalin-2(3H)-one (100 mg, 0.436 mmol), 1-(3-chloroproxy)-4-fluorobenzene (100 μL, 0.65 mmol) and KI (144 mg, 0.87 mmol) in DMF (2 mL) is degassed with argon for 3 minutes and DIPEA (150 μL, 0.87 mmol) is added. The resulting mixture is heated to 78° C. and stirred at this temperature for 2 h. The mixture is cooled to room temperature and then filtered. The filter cake is purified by silica gel column chromatography using a gradient of 0-100% ethyl acetate in a mixture of methanol/7N $NH_3$ in methanol (1:0.1 v/v) as an eluent to produce partially purified product, which is further purified with a semi-preparative HPLC system using a gradient of 0-60% acetonitrile in water containing 0.1% formic acid over 16 min to obtain the title product as a solid (50 mg, yield 30%). MS (ESI) m/z 406.2 [M+1]$^+$. $^1$H NMR (500 MHz, DMSO-$d_6$) δ 10.3 (s, 1H), 7.2-7.1 (m, 2H), 7.0-6.9 (m, 2H), 6.8 (dd, J=1.03, 7.25 Hz, 1H), 6.6 (t, J=7.55 Hz, 1H), 6.6 (dd, J=1.07, 7.79 Hz, 1H), 4.0 (t, J=6.35 Hz, 2H), 3.8 (d, J=14.74 Hz, 1H), 3.3-3.2 (m, 3H), 2.9 (dd, J=6.35, 11.13 Hz, 1H), 2.7-2.6 (m, 1H), 2.5-2.3 (m, 2H), 2.1 (t, J=11.66 Hz, 1H), 2.0 (d, J=14.50 Hz, 1H), 1.9-1.8 (m, 3H), 1.7 (t, J=11.04 Hz, 1H).

Example 2: Receptor Binding Profile of Compound of Ex. 1

Receptor binding is determined for the Compound of Example 1, using the compound of Formula A as a control.

The following literature procedures are used, each of which reference is incorporated herein by reference in their entireties: 5-HT$_{2A}$: Bryant, H. U. et al. (1996), *Life Sci.*, 15:1259-1268; D2: Hall, D. A. and Strange, P. G. (1997), *Brit. J. Pharmacol.*, 121:731-736; D1: Zhou, Q. Y. et al. (1990), *Nature*, 347:76-80; SERT: Park, Y. M. et al. (1999), *Anal. Biochem.*, 269:94-104; Mu opiate receptor: Wang, J. B. et al. (1994), *FEBS Lett.*, 338:217-222.

In general, the results are expressed as a percent of control specific binding:

$$\frac{\text{measured specific binding}}{\text{control specific binding}} \times 100$$

and as a percent inhibition of control specific binding:

$$100 - \left(\frac{\text{measured specific binding}}{\text{control specific binding}} \times 100\right)$$

obtained in the presence of the test compounds.

The IC$_{50}$ values (concentration causing a half-maximal inhibition of control specific binding) and Hill coefficients (nH) are determined by non-linear regression analysis of the competition curves generated with mean replicate values using Hill equation curve fitting:

$$Y = D + \left[\frac{A - D}{1 + (C/C_{50})^{nH}}\right]$$

where Y=specific binding, A=left asymptote of the curve, D=right asymptote of the curve, C=compound concentration, C$_{50}$=IC$_{50}$, and nH=slope factor. This analysis was performed using in—house software and validated by comparison with data generated by the commercial software SigmaPlot® 4.0 for Windows® (© 1997 by SPSS Inc.). The inhibition constants (Ki) were calculated using the Cheng Prusoff equation:

$$Ki = \frac{IC_{50}}{(1 + L/K_D)}$$

where L=concentration of radioligand in the assay, and K$_D$=affinity of the radioligand for the receptor. A Scatchard plot is used to determine the K$_D$.

The following receptor affinity results are obtained, using the tosylate salt of a Compound of Formula A as a control:

| Receptor | Example 1 | Formula A (tosylate salt) |
|---|---|---|
| | Ki (nM) or maximum inhibition | |
| 5-HT$_{2A}$ | 8.3 | 10 |
| D2 | 160 | 49 |
| D1 | 50 | 41 |
| SERT | 590 | 16 |

| Receptor | Example 1 | Formula A (tosylate salt) |
|---|---|---|
| | Ki (nM) or maximum inhibition | |
| Mu opiate receptor | 11 | >10,000 |
| Delta opioid | No inhibition | |
| Kappa opioid | 16% @ 100 nM | |
| NOP (Nociceptin Receptor) | No inhibition | |

Example 3: DOI-Induced Head Twitch Model in Mice

R-(−)-2,5-dimethoxy-4-iodoamphetamine (DOI) is an agonist of the serotonin 5-HT$_2$ receptor family. When administered to mice, it produces a behavioral profile associated with frequent head twitches. The frequency of these head twitches during a predetermined period of time can be taken as an estimate of 5-HT$_2$ receptor agonism in the brain. Conversely, this behavioral assay can be used to determine 5-HT$_2$ receptor antagonism in the brain by administering the DOI with or without an antagonist and recording the reduction in DOI-induced head twitches after the administration of the antagonist.

The method of Darmani et al., *Pharmacol Biochem Behav.* (1990) 36:901-906 (the contents of which are incorporated by reference in their entirety) is used with some modifications. (±)-DOI HCl is injected subcutaneously and the mice are immediately placed in a conventional plastic cage. The number of head twitches is counted during 6 min, beginning 1 min after DOI administration. The tested compound is administered orally 0.5 hr before the injection of DOI. Results area calculated as the EC50 for reducing DOI-induced head twitches. The results are shown in the following Table:

| Compound | EC$_{50}$ (mg/kg, p.o.) |
|---|---|
| Example 1 | 0.44 |
| Formula A | 0.09 |

The results show that the compounds of Example 1 potently block DOI head twitch, comparable to the reference compounds Formula A.

Example 4: Mouse Tail Flick Assays

The Mouse Tail Flick Assay is a measure of analgesia, indicated by the pain reflex threshold of restrained mice. Male CD-1 mice are positioned with their tails under a focused beam of a high-intensity infrared heat source, resulting in heating of the tail. The animal can withdraw its tail from the heat source at any time that it becomes uncomfortable. The amount of time (latency) between turning on the heating instrument and the flicking of the mouse's tail out of path of the heat source is recorded. Administration of morphine results in analgesia, and this produces a delay in the mouse's reaction to the heat (increased latency). Prior administration of a morphine (MOR) antagonist, i.e., naloxone (NAL), reverses the effect and results in normal latency time. This test is used as a functional assay to gauge antagonism of mu-opiate receptors.

Example 4a: Antagonism of Morphine-Induced Analgesia by Compound of Example 1

Ten male CD-1 mice (about 8 weeks of age) are assigned to each of five treatment groups. The groups are treated as follows: Group (1) [negative control]: administered 0.25% methylcellulose vehicle p.o., 60 minutes before the tail flick test, and saline vehicle 30 minutes before the tail flick test; Group (2) [positive control]: administered 0.25% methylcellulose vehicle p.o., 60 minutes before the test, and 5 mg/kg morphine in saline 30 minutes before the test; Group (3) [positive control]: administered 3 mg/kg naloxone in saline 50 minutes before the test, and 5 mg/kg morphine in saline 30 minutes before the test; Groups (4)-(6): administered either 0.1 mg/kg, 0.3 mg/kg or 1 mg/kg of the test compound in 0.25% methylcellulose vehicle p.o., 60 minutes before the test, and 5 mg/kg morphine in 30 minutes before the test. The results are shown in the following table as mean latency measured in seconds:

|       | Group 1 Veh/Veh | Group 2 Veh/Mor | Group 3 Nal/Mor | Group 4 Cmpd/Mor (0.1 mg/kg) | Group 5 Cmpd/Mor (0.3 mg/kg) | Group 6 Cmpd/Mor (1 mg/kg) |
|-------|-----|-----|-----|-----|-----|-----|
| Ex. 1 | 0.887 | 8.261 | 3.013 | 6.947 | 5.853 | 6.537 |

The results demonstrate that the compound of Example 1 exerts a blockade of morphine-induced mu-opiate receptor-mediated analgesia.

Example 4b: Analgesia by Compound of Example 1, Inhibited by Naloxone

In a second study using the mouse tail flick assay as described above, the compound of Example 1 is further compared at doses of 1.0 mg/kg, 3.0 mg/kg and 10 mg/kg against morphine at 5 mg/kg with and without pre-dosing with naloxone at 3 mg/kg (intraperitoneal). In the pre-treatment groups, the naloxone is administered 20 minutes prior to the tail flick test. In the non-pre-treatment controls, saline is administered 20 minutes prior to the tail flick test. In each group, the vehicle, morphine or compound of Example 1 is administered 30 minutes before the tail flick test. The results are shown in the table below as mean latency in seconds:

|                        | Vehicle | Morphine | Ex. 1 at 1 mg/kg | Ex. 1 at 3 mg/kg | Ex. 1 at 10 mg/kg |
|------------------------|---------|----------|------------------|------------------|-------------------|
| Saline pre-treatment   | 0.9     | 9.8      | 4.1              | 7.4              | 9.8               |
| Naloxone pre-treatment | 0.8     | 1.5      | 1.3              | 1.7              | 2.1               |

It is found that administration of the compound of Example 1 at all doses significantly increased the latency to tail flick, and that this effect is attenuated by pre-treatment with naloxone. The results demonstrate a dose-dependent analgesic effect produced by the Compound of Example 1, and further suggests that this effect is mediated by mu-opioid receptor agonism.

Example 4c: Time Course for Analgesia, Compound of Example 1

The tail flick assay as described above is repeated to determine the time course of analgesia resulting from administration of the compound of Example 1. Mice are administered s.c. either (1) vehicle 30 minutes prior to assay, (2) 5 mg/kg morphine 30 minutes prior to assay, or (3)-(7) the 1 mg/kg of compound of Example 3 30 minutes, 2 hours, 4 hours, 8 hours or 24 hours prior to assay. The results are shown in the table below as mean latency in seconds:

| Treatment | TF Latency (s) |
|-----------|----------------|
| Vehicle, 30 min prior | 1.30 |
| Morphine, 30 min prior | 7.90 |
| Cmpd. Ex. 1, 30 min prior | 5.77 |
| Cmpd. Ex. 1, 2 h prior | 2.42 |
| Cmpd. Ex. 1, 4 h prior | 1.48 |
| Cmpd. Ex. 1, 8 h prior | 1.36 |
| Cmpd. Ex. 1, 24 h prior | 1.29 |

The results show that the Compound of Example 1 produces effective analgesia when administered 30 minutes or 2 hours prior to the tail flick assay (ANOVA, $P<0.001$ vs. vehicle). When administered 4 hours, 8 hours, or 24 hours prior to the tail flick assay, the compound of Example 1 at 1 mg/kg does not produce an analgesic effect significantly different from the vehicle control. Thus, the compound of Example 1 does not produce prolonged analgesia, which means that it would have a lower potential for abuse and a lower risk of drug-drug interactions compared to other opiate analgesics.

Example 4d: Analgesia from Chronic Administration of the Compound of Example 1

The tail flick assay described above is repeated using a test model in which animals receive a 14-day chronic treatment regimen, followed by an acute treatment 30 minutes prior to the tail flick assay. The mice are divided into three broad groups with six sub-groups of 10 mice each. The three groups receive as the chronic treatment either (A) vehicle, (B) compound of Example 1 at 0.3 mg/kg, or (C) compound of Example 1 at 3.0 mg/kg. Each sub-group further receives as the acute treatment either (1) vehicle, or (2)-(6) the compound of Example 1 at 0.01, 0.03, 0.1, 0.3 or 1.0 mg/kg. All treatments are administered s.c. The results are shown in the table below as mean latency to tail flick in seconds:

| Group | Chronic Treatment | Acute Treatment | Latency (s) |
|-------|-------------------|-----------------|-------------|
| (A)   | Vehicle           | Vehicle         | 1.09        |
|       | Vehicle           | Ex. 1, 0.01 mg/kg | 1.87      |
|       | Vehicle           | Ex. 1, 0.03 mg/kg | 2.50      |
|       | Vehicle           | Ex. 1, 0.1 mg/kg  | 5.26      |
|       | Vehicle           | Ex. 1, 0.3 mg/kg  | 8.26      |
|       | Vehicle           | Ex. 1, 1.0 mg/kg  | 9.74      |
| (B)   | Ex. 1, 0.3 mg/kg  | Vehicle           | 0.893     |
|       | Ex. 1, 0.3 mg/kg  | Ex. 1, 0.01 mg/kg | 1.66      |
|       | Ex. 1, 0.3 mg/kg  | Ex. 1, 0.03 mg/kg | 1.30      |
|       | Ex. 1, 0.3 mg/kg  | Ex. 1, 0.1 mg/kg  | 2.60      |
|       | Ex. 1, 0.3 mg/kg  | Ex. 1, 0.3 mg/kg  | 3.93      |
|       | Ex. 1, 0.3 mg/kg  | Ex. 1, 1.0 mg/kg  | 5.64      |

| Group | Chronic Treatment | Acute Treatment | Latency (s) |
|---|---|---|---|
| (C) | Ex. 1, 3.0 mg/kg | Vehicle | 1.04 |
| | Ex. 1, 3.0 mg/kg | Ex. 1, 0.01 mg/kg | 1.64 |
| | Ex. 1, 3.0 mg/kg | Ex. 1, 0.03 mg/kg | 1.80 |
| | Ex. 1, 3.0 mg/kg | Ex. 1, 0.1 mg/kg | 3.94 |
| | Ex. 1, 3.0 mg/kg | Ex. 1, 0.3 mg/kg | 4.84 |
| | Ex. 1, 3.0 mg/kg | Ex. 1, 1.0 mg/kg | 7.94 |

It is found that 0.1, 0.3 and 1.0 mg/kg acute treatment with the compound of Example 1 produces a statistically significant dose-dependent analgesic effect compared to in-group acute treatment with vehicle. This is true for each of the chronic groups (A), (B) and (C). As compared to pre-treatment with vehicle, pre-treatment with the compound of Example 1 at 0.3 mg/kg or 3.0 mg/kg generally showed a statistically significant decrease in tail flick latency when the same acute treatment subgroups are compared. These results demonstrate that while some tolerance to the analgesic effect of the compound of Example 3 occurs after 14-days of chronic treatment, the analgesia obtained remains effective despite chronic pre-treatment.

Example 5: Mu-Opiate Receptor Activity Assays

The compound of Example 1 is tested in CHO-K1 cells expressing hOP3 (human mu-opiate receptor µ1 subtype) using an HTRF-based cAMP assay kit (cAMP Dynamic2 Assay Kit, from Cisbio, #62AM4PEB). Frozen cells are thawed in a 37° C. water bath and are resuspended in 10 mL of Ham's F-12 medium containing 10% FBS. Cells are recovered by centrifugation and resuspended in assay buffer (5 nM KCl, 1.25 mM $MgSO_4$, 124 mM NaCl, 25 mM HEPES, 13.3 mM glucose, 1.25 mM $KH_2PO_4$, 1.45 mM $CaCl_2$), 0.5 g/L protease-free BSA, supplemented with 1 mM IBMX). Buprenorphine, a mu-opiate receptor partial agonist, and naloxone, a mu-opiate receptor antagonist, and DAMGO, a synthetic opioid peptide full agonist, are run as controls.

For agonist assays, 12 µL of cell suspension (2500 cells/well) are mixed with 6 µL forksolin (10 µM final assay concentration), and 6 µL of the test compound at increasing concentrations are combined in the wells of a 384-well white plate and the plate is incubated for 30 minutes at room temperature. After addition of lysis buffer and one hour of further incubation, cAMP concentrations are measured according to the kit instructions. All assay points are determined in triplicate. Curve fitting is performed using XLfit software (IDBS) and $EC_{50}$ values are determined using a 4-parameter logistic fit. The agonist assay measures the ability of the test compound to inhibit forskolin-stimulated cAMP accumulation.

For antagonist assays, 12 µL of cell suspension (2500 cells/well) are mixed with 6 µL of the test compound at increasing concentrations, and combined in the wells of a 384-well white plate and the plate is incubated for 10 minutes at room temperature. 6 µL of a mixture of DAMGO (D-Ala$^2$-N-MePhe$^4$-Gly-ol-enkephalin, 10 nM final assay concentration) and forskolin (10 µM final assay concentration) are added, and the plates are incubated for 30 minutes at room temperature. After addition of lysis buffer, and one hour of further incubation, cAMP concentrations are measured according to the kit instructions. All assay points are determined in triplicate. Curve fitting is performed using XLfit software (IDBS) and $IC_{50}$ values are determined using a 4-parameter logistic fit. Apparent dissociation constants ($K_B$) are calculated using the modified Cheng-Prusoff equation. The antagonist assay measures the ability of the test compound to reverse the inhibition of forskolin-induced cAMP accumulation caused by DAMGO.

The results are shown the Table below. The results demonstrate that the compound of Example 1 is a weak antagonist of the Mu receptor, showing much higher $IC_{50}$ compared to naloxone, and that it is a moderately high affinity, but partial agonist, showing only about 22% agonist activity relative to DAMGO (as compared to about 79% activity for buprenorphine relative to DAMGO). The compound of Example 1 is also shown to have moderately strong partial agonist activity.

| Compound | Antagonist IC50 (nM) | Agonist EC50 (nM) | $K_B$ (nM) |
|---|---|---|---|
| Naloxone | 5.80 | — | 0.65 |
| DAMGO | — | 1.56 | — |
| Buprenorphine | — | 0.95 | — |
| Cmpd. Ex. 1 | 641 | 64.5 | 71.4 |

Buprenorphine is a drug used for chronic pain treatment and for opiate withdrawal, but it suffers from the problem that users can become addicted due to its high partial agonist activity. To offset this, the commercial combination of buprenorphine with naloxone is used (sold as Suboxone). Without being bound by theory, it is believed that the compounds of the present invention, which are weaker partial Mu agonists than buprenorphine, with some moderate antagonistic activity, will allow a patient to be more effectively treated for pain and/or opiate withdrawal with lower risks of addiction.

In additional related study using a recombinant human MOP-beta-arresting signaling pathway, it is found that the Compound of Example 1 does not stimulate beta-arrestin signaling via the MOP receptor at concentrations up to 10 µM, but that it is an antagonist with an $IC_{50}$ of 0.189 µM. In contrast, the full opioid agonist Met-enkephalin stimulates beta-arrestin signaling with an $EC_{50}$ of 0.08 µM.

Example 6: The Compound of Formula a, Via its D1-Receptor Activity, has been Shown to Enhance NMDA and AMPA Currents in Rat mPFC, and to Stimulate mTOR Signaling The Compound of Formula A, like the Compounds of Formula I, and the compound of Example 1, are both active at the D1 receptor. The Compound of Formula A has a D1 receptor Ki of 41 nM, while the compound of Example 1 has a D1 receptor Ki of 50 nM. As a result, it is believed that the compound of Example 1 has similar effects on NMDA, AMPA and mTOR signaling as the Compound of Formula A.

It is known that upstream and downstream effectors of the mTOR (e.g., mTORC1) signaling pathway are increased in the mPFC (medial pre-frontal cortex) of rats 1 hour and 24 hours after administration of the rapid-acting antidepressant ketamine. Ketamine is thus used as a positive control and compared to the effects of Compound of Formula A on the same signaling pathway. In this study, Compound of Formula A is given at different doses ranging from 1 to 8 mg/kg (i.p.) to adult rats and brain samples are analyzed 60 min, 90 min or 24 hours later. Results show that, like ketamine (30 mg/kg), the Compound of Formula A rapidly activates the mTORC1 signaling pathway in mPFC, and particularly in those intracellular cascades involved in synaptic plasticity (i.e., p-Akt thr308 and p-P70S6K). More precisely, the Compound of Formula A has a longer lasting effect compared with ketamine (30 mg/kg) on phospho-protein levels at 24 hours, which is consistent with the longer-lasting pharmacokinetic profile of lumateperone in vivo.

The Compound of Formula A, given alone, uniquely enhances both NMDA and AMPA receptor currents in mPFC neurons via activation of D1 receptors. The Compound of Formula A, alone, in a bath applied to rat mPFC slices (3-100 nM) enhanced NMDA and AMPA currents 5 min later measured using intracellular whole-cell patch clamp techniques (Björkholm et al., 2015). The effect of the Compound of Formula A (30 nM) (*p<0.05; **p<0.01, t-test) is fully blocked in the presence of the D1 receptor antagonist, SCH-23390 (1 µM) (*p<0.05; **p<0.01; ##, p<0.01, t-test). Combined administration of the antipsychotic, olanzapine, and the SSRI, fluoxetine, similarly induces rapid antidepressant activity in humans and animals (Tohen et al., 2010); likewise, combined application of olanzapine and fluoxetine is required to induce AMPA receptor currents in vitro.

Results show that while the Compound of Formula A at 30 nM concentration produces almost 150% increased NMDA-induced currents in rat mPFC compared to control, the combination of the Compound of Formula A (30 nM) and SCH 23390 (1 µM) results in a reduction in NMDA-induced currents compared to control (about 90% of control). Substantially the same results are observed for AMPA-induced currents. In contrast, the antipsychotic drug olanzapine, is found to enhance AMPA-induced currents only in the presence of the SSRI fluoxetine. 3 nM olanzapine alone results in about 100% of the AMPA-induced current of the control, while 100 nM fluoxetine results in about 90% of the AMPA-induced current of the control. However, the combination of 3 nM olanzapine and 100 nM fluoxetine is found to synergistically result in almost 150% of the AMPA-induced current of control. When SCH 23390 (1 µM) is combined with the olanzapine and fluoxetine, however, the AMPA-induced current returns to approximately 100% of the control level.

The effects of the Compound of Formula A and ketamine on the phosphorylation of mTOR pathway proteins in rat PFC at 24 hours post-administration has also been studied. In this experiment, rats (N=8/group) are treated with one intraperitoneal injection (acutely) with either 30 mg/kg ketamine, or 3 mg/kg the Compound of Formula A in a vehicle of: 5% DMSO, 5% Tween20, 15% PEG400 and 75% water, and sacrificed 24 h later. Pre-frontal cortical phosphorylation levels of AKT (at Threonine 308), mTOR (at Serine 2448) or P70s6 kinase (at Threonine 389) are evaluated after normalization to total protein levels for each target, at both 1 hour and 24 hours. It is found that both the Compound of Formula A and ketamine increase phosphorylation of AKT at thr308 at both 1 hour and 24 hours post-administration (approx. a 50% increase in phosphorylation). Neither ketamine nor the Compound of Formula A results in a change in mTOR phosphorylation. Ketamine is found to transiently increase p70s6K phosphorylation, an effect which attenuates over the 24-time period, whereas the Compound of Formula A progressively increases p7-s6K phosphorylation over the 24 hour period. Overall, these results show the Compound of Formula A alters the mTORC1 signaling pathways in the same way as ketamine, but with more prolonged effects.

The Compound of Formula A thus enhances both NMDA and AMPA-induced currents in mPFC pyramidal neurons via activation of D1 receptors. These changes have been implicated in the mechanism of action of rapid-acting antidepressants. The Compound of Formula A alone activates AMPA-type receptor currents in mPFC in a manner previously reported only after combined application of an antipsychotic drug (e.g., olanzapine, asenapine, brexpiprazole, or risperidone) and a selective serotonin reuptake inhibitor (SSRI; fluoxetine or citalopram), or after ketamine, which also exhibits rapid onset antidepressant activity in humans.

Additionally, the Compound of Formula A, like ketamine, increases protein phosphorylation of key proteins in the mTOR pathway, including the protein kinase, Akt, and p70S6 kinase, further supporting activation of a common pathway by lumateperone and ketamine. Clinically, combined adjunctive treatment with a low-dose of APD (e.g., olanzapine, quetiapine, or aripiprazole), and an SSRI, like fluoxetine, induces rapid, sustained antidepressant effects in patients with TRD. These data support that the Compound of Formula A achieves enhanced glutamatergic neurotransmission, owing to multiple pharmacological properties, including its uniquely potent activity (among antipsychotic medications) as a SERT inhibitor and its ability to enhance dopamine neurotransmission via D1 receptors.

Together these studies further elucidate the signaling pathways that underlie the Compound of Formula A administration, supporting a fast-acting antidepressant action via indirect dopamine D1 receptor-dependent enhancement of NMDA and AMPA currents coupled with activation of the mTORC1 signaling pathway. Based on these data the Compound of Formula A may be useful as a single, stand-alone, orally-available, rapid-acting treatment for depression and anxiety, lacking the adverse side effects of ketamine and other current pharmacological approaches.

The Compounds of Formula I, as disclosed herein, and the compound of Example 1 in particular, are expected to have these same fast-acting antidepressant properties based on D1 receptor-dependent enhancement of NMDA and AMPA currents coupled with activation of the mTORC1 signaling pathway.

We claim:

1. A method for the treatment of acute depression or acute anxiety comprising administering to a patient in need thereof, a therapeutically effective amount of a Compound of Formula I:

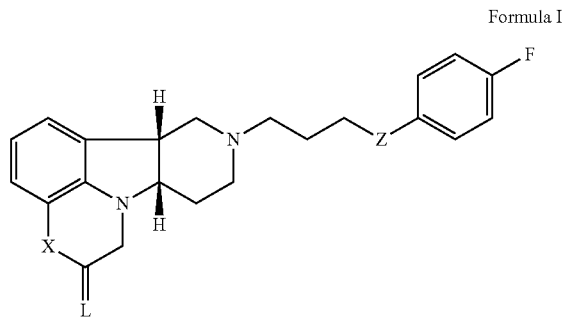

Formula I wherein:
X is —N(H)—, —N(CH$_3$)— or —O—;
L is O;
Z is —O—;
in free, or pharmaceutically acceptable salt form;
wherein the patient shows an acute response to treatment within less than 3 weeks.

2. The method according to claim 1, wherein X in the compound of Formula I is —N(H)—, or —N(CH₃)—.

3. The method according to claim 2, wherein X in the compound of Formula I is —N(H)—.

4. The method according to claim 1, wherein the Compound of Formula I is:

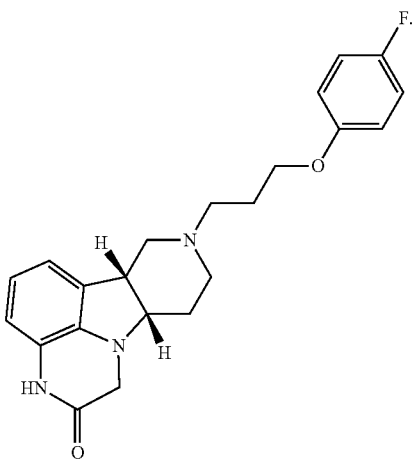 [SMILES: O=C1CN2c3c(cccc3[C@@H]3CN(CCCOc4ccc(F)cc4)CC[C@@H]32)N1]

5. The method according to claim 4, wherein the Compound of Formula I is in the form of the tosylate salt.

6. The method according to claim 1, wherein the method comprises once daily administration of a unit dosage comprising the compound of Formula I in tosylate salt form in an amount equivalent to 1 to 100 mg of free base, and a pharmaceutically acceptable diluent or carrier.

7. The method according to claim 1, wherein the condition to be treated is acute anxiety.

8. The method according to claim 1, wherein the condition to be treated is acute depression.

9. The method according to claim 1, wherein the condition to be treated is treatment resistant depression.

10. The method according to claim 1, wherein the Compound of Formula I is in combination with an effective amount of an additional anxiolytic or antidepressant agent.

11. The method according to claim 10, wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics.

12. The method according to claim 1, wherein the method enhances mTOR signaling.

13. The method according to claim 1, wherein the method reduces neuroinflammation.

14. The method according to claim 1, wherein the compound of Formula I is administered intra-nasally, subcutaneously, intravenously, orally, sub-lingually, intra-peritoneally, or buccally.

15. The method according to claim 1, wherein the method further comprises the concurrent administration of an NMDA receptor antagonist.

16. The method according to claim 1, wherein the method further comprises the concurrent administration of a NMDA receptor allosteric modulator.

17. The method according to claim 1, wherein the patient has not responded to, or has not responded adequately to, or who suffers undesirable side effects from, treatment with another antidepressant agent.

18. The method according to claim 1, wherein the Compound of Formula I is administered as monotherapy.

19. The method according to claim 1, wherein the method does not put the patient at risk for sedation, dissociation, abuse, misuse, or suicidal ideation, or does not result in hypertension within four hours after administration of a dose of the Compound of Formula I.

20. The method according to claim 7, wherein the acute anxiety is selected from-short-duration anxious episode associated with generalized anxiety disorder, panic disorder, specific phobias, or social anxiety disorder, and social avoidance.

21. The method according to claim 8, wherein the acute depression is selected from acute major depressive episode, acute short-duration depressive episode, and acute recurrent brief depressive episode.

22. The method according to claim 9, wherein the treatment resistant depression is depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof.

23. The method according to claim 17, wherein the patient has not responded to, or has not responded adequately to, or who suffers undesirable side effects from, treatment with another antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), and a serotonin receptor antagonist.

24. The method according to claim 1, wherein the patient shows an acute response to treatment within 1 to 7 days.

25. The method according to claim 1, wherein the patient shows an acute response to treatment within less than 1 week.

26. The method according to claim 1, wherein the patient shows an acute response to treatment within less than 2 days.

* * * * *

UNITED STATES PATENT AND TRADEMARK OFFICE
CERTIFICATE OF CORRECTION

Page 1 of 3

PATENT NO. : 12,023,331 B2
APPLICATION NO. : 17/115416
DATED : July 2, 2024
INVENTOR(S) : Snyder et al.

It is certified that error appears in the above-identified patent and that said Letters Patent is hereby corrected as shown below:

In the Specification

Column 8, Line 31, "at least 2λ" should be changed to "at least 2×"

Column 11, Lines 11-27, " 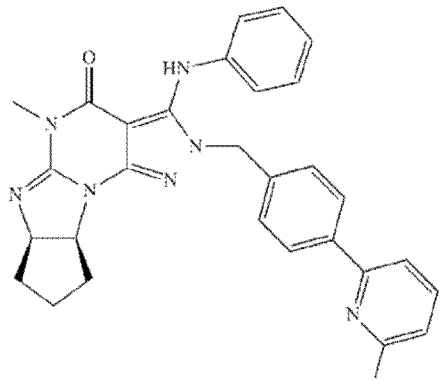 " should be changed to

" 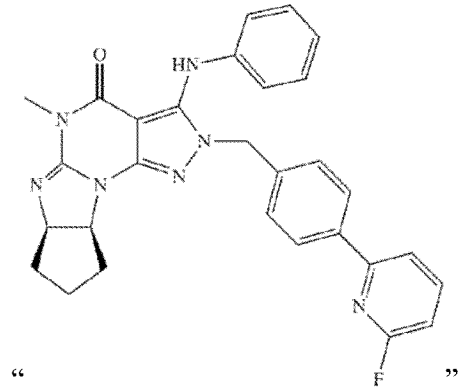 "

Signed and Sealed this
Twelfth Day of August, 2025

Coke Morgan Stewart
*Acting Director of the United States Patent and Trademark Office*

CERTIFICATE OF CORRECTION (continued)
U.S. Pat. No. 12,023,331 B2

Page 2 of 3

Column 12, Lines 3-20, " 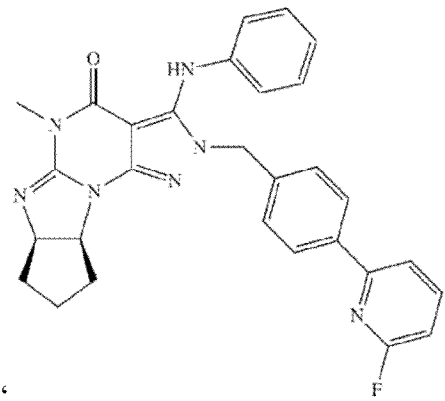 " should be changed to

" 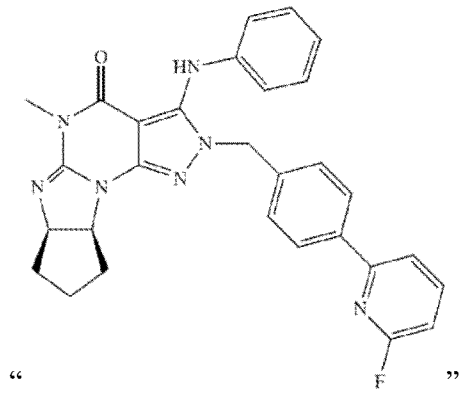 "

Column 16, Line 64, "at least 2λ" should be changed to "at least 2×"

Column 25, Line 31, "at least 2λ" should be changed to "at least 2×"

Column 28, Lines 27-45, " 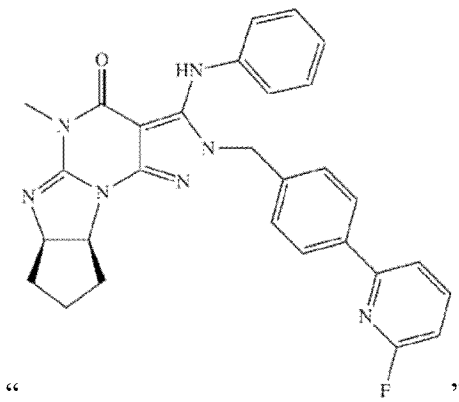 " should be changed to

CERTIFICATE OF CORRECTION (continued)
U.S. Pat. No. 12,023,331 B2

"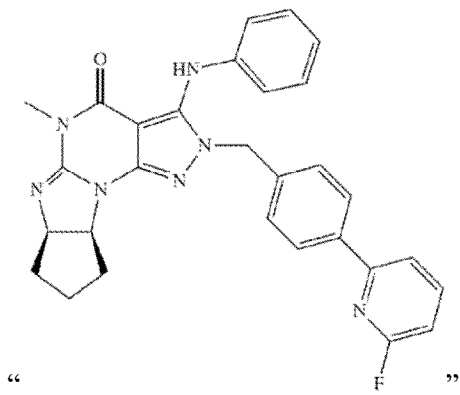"

Column 44, Line 43, "Formula a" should be changed to "Formula A"